United States Patent
Li et al.

(10) Patent No.: US 11,020,205 B2
(45) Date of Patent: Jun. 1, 2021

(54) PROVIDING A SIMULATED OUTCOME OF DENTAL TREATMENT ON A PATIENT

(71) Applicant: Align Technology, Inc., San Jose, CA (US)

(72) Inventors: Yingjie Li, Cary, NC (US); Chao Shi, Morrisville, NC (US); Zelko Relic, Pleasanton, CA (US); Michael Alan Stocks, Holly Springs, NC (US); Andrey Bushev, Morrisville, NC (US); Ya Xue, Chapel Hill, NC (US); Eric P. Meyer, Pleasanton, CA (US)

(73) Assignee: Align Technology, Inc., San Jose, CA (US)

( * ) Notice: Subject to any disclaimer, the term of this patent is extended or adjusted under 35 U.S.C. 154(b) by 209 days.

(21) Appl. No.: 16/400,980

(22) Filed: May 1, 2019

(65) Prior Publication Data

US 2020/0000551 A1    Jan. 2, 2020

Related U.S. Application Data

(60) Provisional application No. 62/692,494, filed on Jun. 29, 2018.

(51) Int. Cl.
*A61C 7/00* (2006.01)
*G16H 50/50* (2018.01)
(Continued)

(52) U.S. Cl.
CPC ............ *A61C 7/002* (2013.01); *A61C 9/0053* (2013.01); *G16H 50/50* (2018.01);
(Continued)

(58) Field of Classification Search
CPC . A61C 7/002; A61C 9/0053; A61C 2007/004; A61C 13/0004; G16H 50/50; B33Y 80/00; B33Y 50/00; G09B 23/283
See application file for complete search history.

(56) References Cited

U.S. PATENT DOCUMENTS

| 2,467,432 A | 4/1949 | Kesling et al. |
| 3,407,500 A | 10/1968 | Kesling et al. |

(Continued)

FOREIGN PATENT DOCUMENTS

| AU | 3031677 A | 5/1979 |
| AU | 517102 B2 | 7/1981 |

(Continued)

OTHER PUBLICATIONS

PCT/US2019/030266 International Search Report and Written Opinion dated Jul. 30, 2019. 13 pages.

(Continued)

*Primary Examiner* — Brenda C Bernardi
(74) *Attorney, Agent, or Firm* — Wilson Sonsini Goodrich & Rosati

(57) ABSTRACT

Systems and methods of simulating dental treatments are disclosed. A method may include capturing a first 2D image of a patient's face, including the patient's teeth, building a parametric 3D model of the patient's teeth based on the 2D image, developing a simulated outcome of a dental treatment of the patient's teeth by rendering the 3D model with the patient's teeth in one or more positions and/or orientations corresponding to the treatment goals of the dental treatment plan, and rendering a second 2D image of the patient's face with teeth according to a simulated outcome of the dental treatment plan. As noted herein, the dental treatment plan may include orthodontic and/or restorative elements. The simulated outcome may correspond to estimated outcomes and/or intended outcomes of the dental treatment plan.

21 Claims, 21 Drawing Sheets

(51) Int. Cl.
  *A61C 9/00* (2006.01)
  *B33Y 50/00* (2015.01)
  *B33Y 80/00* (2015.01)
  *A61C 13/00* (2006.01)
  *G09B 23/28* (2006.01)

(52) U.S. Cl.
  CPC .... *A61C 13/0004* (2013.01); *A61C 2007/004* (2013.01); *B33Y 50/00* (2014.12); *B33Y 80/00* (2014.12); *G09B 23/283* (2013.01)

(56) References Cited

U.S. PATENT DOCUMENTS

| | | |
|---|---|---|
| 3,600,808 A | 8/1971 | Reeve et al. |
| 3,660,900 A | 5/1972 | Andrews et al. |
| 3,683,502 A | 8/1972 | Wallshein et al. |
| 3,738,005 A | 6/1973 | Cohen et al. |
| 3,860,803 A | 1/1975 | Levine et al. |
| 3,916,526 A | 11/1975 | Schudy et al. |
| 3,922,786 A | 12/1975 | Lavin et al. |
| 3,950,851 A | 4/1976 | Bergersen et al. |
| 3,983,628 A | 10/1976 | Acevedo et al. |
| 4,014,096 A | 3/1977 | Dellinger et al. |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van Der Zel et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,011,405 A | 4/1991 | Lemchen |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,202 A | 8/1994 | Deshayes et al. |
| 5,368,478 A | 11/1994 | Andreiko et al. |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,934,288 A | 8/1999 | Avila et al. |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda et al. |
| 6,049,743 A | 4/2000 | Baba et al. |
| 6,062,861 A | 5/2000 | Andersson |
| 6,068,482 A | 5/2000 | Snow et al. |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier et al. |
| 6,398,548 B1 | 6/2002 | Muhammad et al. |

(56) References Cited

U.S. PATENT DOCUMENTS

| | | |
|---|---|---|
| 6,402,707 B1 | 6/2002 | Ernst et al. |
| 6,450,807 B1 | 9/2002 | Chishti et al. |
| 6,482,298 B1 | 11/2002 | Bhatnagar et al. |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,830,450 B2 | 12/2004 | Knopp et al. |
| 2002/0006597 A1 | 1/2002 | Andreiko et al. |
| 2003/0009252 A1 | 1/2003 | Pavlovskaia et al. |
| 2003/0139834 A1* | 7/2003 | Nikolskiy ............... G16H 50/50 700/98 |
| 2003/0224311 A1 | 12/2003 | Cronauer et al. |
| 2004/0029068 A1 | 2/2004 | Sachdeva et al. |
| 2004/0128010 A1 | 7/2004 | Pavlovskaia et al. |
| 2005/0055118 A1 | 3/2005 | Nikolskiy et al. |
| 2007/0134613 A1 | 6/2007 | Kuo et al. |
| 2012/0015316 A1* | 1/2012 | Sachdeva ................. A61C 5/77 433/24 |
| 2018/0263733 A1* | 9/2018 | Pokotilov ............... G06T 17/20 |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-2018112427 A1 | 6/2018 |
| WO | WO-2020005386 A1 | 1/2020 |

OTHER PUBLICATIONS

AADR. American Association for Dental Research, Summary of Activities, Mar. 20-23, 1980, Los Angeles, CA, p. 195.

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28- 36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy. swin.edu.au/—pbourke/prolection/coords>.

Boyd et al., "Three Dimensional Diagnosis and Orthodontic Treatment of Complex Malocclusions With the Invisalign Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

Cardinal Industrial Finishes, Powder Coatings information posted at<http://cardinalpaint.com> on Aug. 25, 2000, 2 pages.

Carnaghan, "An Alternative to Holograms for the Portrayal of Human Teeth," 4th Int'l. Conf. on Holographic Systems, Components and Applications, Sep. 15, 1993, pp. 228-231.

(56) References Cited

OTHER PUBLICATIONS

Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally, Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
DENT-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98-Conference Program, retrieved from the Internet< http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management,"J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-228 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.

(56) References Cited

OTHER PUBLICATIONS

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
Mccann, "Inside the ADA," J. Amer. Dent. Assoc., 118:286-294 (Mar. 1989).
Mcnamara et al., "Invisible Retainers," J. Cfin. Orthod., pp. 570-578 (Aug. 1985).
Mcnamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/PRO Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art'?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).

(56) References Cited

OTHER PUBLICATIONS

Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 388-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pages (2002).
Co-pending U.S. Appl. No. 17/020,550, filed Sep. 14, 2020.

* cited by examiner

PROVIDING A SIMULATED OUTCOME OF DENTAL TREATMENT ON A PATIENT

CROSS REFERENCE

This application claims the benefit of U.S. Provisional Patent Application No. 62/692,494, filed Jun. 29, 2018, the disclosure of which is herein incorporated by reference in its entirety.

TECHNICAL FIELD

The technical field relates to digital dental technologies, and more particularly to providing a simulated outcome of dental (e.g., orthodontic, restorative, etc.) treatment by evaluating a two-dimensional (2D) depiction of a patient's untreated teeth against parameters associated with model tooth arches.

BACKGROUND

Orthodontic treatment often includes addressing issues with malpositioned teeth and/or jaws and may include diagnosis, prevention, and/or correction of malocclusions. A person seeking orthodontic treatment may seek a treatment plan from an orthodontist, such as a professional who has undergone special training after graduating from dental school. Many orthodontic treatment plans include treatment with braces, brackets, wires, and/or polymeric appliances. A person seeking orthodontic treatment may have orthodontic appliances adjusted at various times by an orthodontic professional who designs and/or implements the orthodontic appliances.

Many people are referred for orthodontic treatment by dentists, other treatment professionals, or other people. For instance, many teenage patients or people with severe malocclusions may be referred for orthodontic treatment by their dentists or parents. However, many other people may not know whether or not they should receive orthodontic treatment. As an example, many individuals with mild malocclusions may not know whether or not orthodontic treatment is appropriate or desirable for them.

Additionally, many people may wish to visualize examples of their smiles without malpositioned teeth and/or jaws, e.g., after estimated and/or intended dental treatment(s), after insertion of implants or other devices, with configurations that would be appropriate for their face, age, heritage, and/or lifestyle, etc. While it may be desirable to provide people with the ability to visualize how their smiles and/or faces would look after possible treatment options, the computational burdens and/or costs of existing tools make it hard to do so. Existing tools also make it hard to visualize how dental treatment would meaningfully impact patients' lives.

SUMMARY

This disclosure generally relates to systems, methods, and/or computer-readable media related to simulating dental treatment of a patient's teeth, and particularly to providing a more photo-realistic rendering of a two-dimensional (2D) image of a patient that represents one or more simulated (e.g., estimated and/or intended) outcomes of a dental treatment plan. The implementations herein produce near accurate and realistic renderings of simulated outcomes of dental treatment and/or animations of three-dimensional (3D) models that could previously have not been generated, or generated only in a rudimentary fashion through manual photo editing tools. As noted herein, the implementations described use automated agents and/or rules to provide accurate and realistic renderings of simulated outcomes of dental (e.g., orthodontic, restorative, etc.) treatment and/or animations of 3D models that were previously not possible. The implementations herein allow people considering and/or undergoing orthodontic treatment the ability to visualize on a computer automatically generated simulated orthodontic treatment outcome simulations, and may inform a person's choices as to whether or not to seek orthodontic treatment in general and/or specific courses of orthodontic treatment. As noted herein, the disclosure also relates to systems and methods of accurately and realistically simulating 3D models of teeth in final orthodontic positions in a 2D image of person.

A computer-implemented method of simulating one or more simulated outcomes of dental treatment is disclosed. In some embodiments, the computer-implemented method of simulating orthodontic treatment may include capturing a first 2D image. In some embodiments, the first 2D image may include a representation of a patient's face and a patient's teeth. The method may include identifying one or more shapes associated with at least one of the patient's teeth. The method may also include building a parametric 3D model of the patient's teeth based on the first 2D image, using one or more case-specific parameters for the one or more shapes associated with the at least one of the patient's teeth. The method may also include simulating an outcome of a dental treatment plan for the patient's teeth to produce a simulated outcome of the dental treatment plan; and modifying the parametric 3D model to provide a modified 3D model representing the simulated outcome of the dental treatment plan. The method may also include rendering, using the modified 3D model, a second 2D image representing the patient's face, wherein the second 2D image represents the patient's teeth in accordance with the simulated outcome of the dental treatment plan.

In some embodiments, building the parametric 3D model includes finding edges of teeth and lips in the first 2D image, aligning a parametric tooth model to the edges of the teeth and lips in the first 2D image to determine the case specific parameters, and storing the case-specific parameters of the parametric tooth model that align the parametric tooth model with the edges of the teeth, gingiva, and lips in the first 2D image.

In some embodiments, rendering the second 2D image includes accessing the parametric 3D model of the patient's teeth, projecting one or more teeth positions from the first 2D image onto the parametric 3D model, and mapping color data from the 2D image to corresponding locations on the parametric 3D model to generate textures for the parametric 3D model, and using the textures as part of the second 2D image of the patient's face.

In some embodiments, the predetermined position is based on an average position of a plurality of previous patients' teeth after dental treatment.

In some embodiments, the predetermined position is based on an average position of a plurality of previous patients' teeth before dental treatment.

In some embodiments, the computer-implemented method may include finding edges of teeth and lips in the first 2D image, and aligning the parametric 3D tooth model to the edges of the teeth, gingiva, and lips in the first 2D image.

In some embodiments, the first 2D image may include a profile image representing a profile of the patient's face.

In some embodiments, the simulated outcome of the dental treatment plan may include an estimated outcome of the dental treatment plan.

In some embodiments, the simulated outcome of the dental treatment plan may include an intended outcome of the dental treatment plan.

In some embodiments, the dental treatment plan may include an orthodontic treatment plan, a restorative treatment plan, or some combination thereof.

In some embodiments, capturing the first 2D image may include instructing a mobile phone or a camera to image the patient's face, or gathering the first 2D image from a storage device or a networked system.

In some embodiments, building the parametric 3D model of the patient's teeth based on the 2D image, using one or more case-specific parameters for the one or more shapes associated with the at least one of the patient's teeth may include coarsely aligning teeth represented in the 3D parametric model to the patient's teeth represented in the 2D image, and executing an expectation step to determine a probability that a projection of a silhouette of the 3D parametric model matches one or more edges of the 2D image a first time.

In some embodiments, building the parametric 3D model of the patient's teeth based on the 2D image, using one or more case-specific parameters for the one or more shapes associated with the at least one of the patient's teeth may include executing a maximization step using a small angle approximation to linearize the rigid transformation of the teeth in the 3D model, and executing the expectation step to determine a probability that a projection of a silhouette of the 3D parametric model matches the edges of the 2D image a second time.

In some embodiments, the computer-implemented method may include iterating through the expectation and maximization steps a first plurality of times to with a first subset of parameters, and after iterating through the expectation and maximization steps the first plurality of times with the first subset of parameters of the 3D parametric model, iterating though the expectation and maximization steps the second plurality of times with the first and second subset of parameters.

In some embodiments, the computer-implement method may include capturing a first 2D image of a patient's face, including their teeth. The method may include building a parametric 3D model of the patient's teeth based on the 2D image, the parametric 3D model including case-specific parameters for the shape of at least one of the patient's teeth. The method may also include simulating an estimated (e.g., an estimated final) and/or intended (e.g., an intended final) orthodontic position of the patient's teeth by gathering information about one or more model tooth arches that represent smiles without malpositioned teeth and/or jaws, and by rendering the 3D model with the patient's teeth in a predetermined position (e.g., one corresponding to positions of teeth in the model arches) and rendering a second 2D image of the patient's face with teeth in an estimated orthodontic position.

In some embodiments, building a parametric 3D model includes finding edges of teeth and lips in the first 2D image, aligning a parametric tooth model to the edges of the teeth and lips in the first 2D image to determine the case specific parameters, and storing the case-specific parameters of the parametric tooth model that align the parametric tooth model with the edges of the teeth, gingiva, and lips in the first 2D image.

In some embodiments, rendering the second 2D image includes rendering the parametric model of the patient's according to the position of the teeth in the first 2D image, projecting the 2D image onto the rendered parametric model of the patient's according to the position of the teeth in the first 2D image, and mapping the color data from the 2D image to corresponding locations on the 3D model to generate textures for the 3D model, and rendering the second 2D image of the patient's face with teeth in the estimated orthodontic position with the generated textures.

In some embodiments, rendering the second 2D image further includes applying simulated treatments or viewing customizations to the second 2D image.

In some embodiments, the simulated treatments or viewing customizations may include one or more of changing an edge of the gingiva, replacing a tooth, adjusting a jaw position, or adjusting the color data.

In some embodiments, the predetermined position is based on a combination of (e.g., an average) positions of a plurality of previous patients' teeth after orthodontic treatment and/or without misaligned teeth or jaws.

In some embodiments, the predetermined position is based on a combination of (e.g., an average) positions of a plurality of previous patients' teeth before orthodontic treatment.

In some embodiments, the method may include finding edges of teeth and lips in the first 2D image, and aligning the parametric tooth model to the edges of the teeth, gingiva, and lips in the first 2D image.

In some embodiments, the first 2D image comprises a profile image.

A computer-implemented method of building a 3D model of teeth from a 2D image is disclosed. The method may include capturing a 2D image of a patient's face, including their teeth, determining edges of teeth and gingiva within the first 2D image, fitting the teeth in a 3D parametric model of teeth to the edges of the teeth and gingiva within the first 2D image, the 3D parametric model including case-specific parameters for the shape of the patient's teeth, determining the value of the case-specific parameters of the 3D parametric model based on the fitting.

In some embodiments, the fitting of the teeth in the 3D parametric model of teeth to the edges of the teeth and gingiva within the first 2D image comprises: coarsely aligning the teeth in the 3D parametric model to the teeth in the 2D image, and executing an expectation step to determine a probability that a projection of a silhouette of the 3D parametric model matches the edges of the 2D image.

In some embodiments, the fitting of the teeth in the 3D parametric model of teeth to the edges of the teeth and gingiva within the first 2D image further comprises: executing a maximization step using a small angle approximation to linearize the rigid transformation of the teeth in the model, and executing the expectation step to determine a probability that a projection of a silhouette of the 3D parametric model matches the edges of the 2D image again.

In some embodiments, a computer-implemented method further comprises iterating through the expectation and maximization steps a first plurality of times with a first subset of parameters; and after iterating through the expectation and maximization steps the first plurality of times with the first subset of parameters of the 3D parametric model, iterating through the expectation and maximization steps the second plurality of times with the first and second subset of parameters.

In some embodiments, the first plurality of times is the same as the second plurality of times.

In some embodiments, the first subset of case-specific parameters of the 3D parametric model is one or more of a scale factor, tooth location, and orientation.

In some embodiments, the second subset of parameters of the 3D parametric model are one or more of a tooth shape and tooth location and orientation.

A computer-implemented method of providing a simulated outcome of orthodontic treatment is disclosed. The method may include building a 3D parametric model of an arch, the 3D parametric model comprising generic parameters for tooth shape, tooth position, and tooth orientation, capturing a 2D image of a patient, constructing a case-specific 3D parametric model of the patient's teeth from the 2D image, determining the case-specific parameters of the constructed parametric model, rendering the 3D parametric model of the patient's teeth in an estimated and/or intended final position (e.g., without misaligned teeth and/or jaws), and inserting the rendered 3D model into a 2D image of the patient.

In some embodiments, the constructing of a 3D parametric model of the patient's teeth from the 2D image includes: finding edges of teeth, gingiva, and lips in the first 2D image, and aligning the 3D model parametric to the edges of the teeth, gingiva, and lips in the first 2D image.

In some embodiments, the method further comprises applying textures to the rendered 3D parametric model of the patient's teeth in an estimated and/or intended final position (e.g., without misaligned teeth and/or jaws), wherein the textures are derived from the 2D image of the patient.

In some embodiments, the textures are derived from the 2D image of the patient by: projecting the 2D image onto the rendered parametric model of the patient's according to the position of the teeth in the first 2D image, and mapping the color data from the 2D image to corresponding locations on the 3D model to derive the textures for the 3D model.

In some embodiments, the rendering of the 3D parametric model of the patient's teeth in the estimated and/or intended final position comprises: generating a mean shape of teeth based on the 3D parametric model, adjusting the shape of the teeth in the 3D parametric model based on case-specific tooth shape parameters, positioning the teeth in a mean tooth location and orientation based on a mean location and orientation parameter such that the teeth have a case specific shape and a mean location and orientation, and scaling the arch based on a case-specific arch scaling parameter.

A non-transitory computer readable medium includes instruction that when executed by a processor cause the processor to perform any of the methods described herein.

A system is disclosed. The system may include a photo parameterization engine configured to generate a 3D parametric arch model from a 2D image of a patient's face and teeth, the parametric 3D model including case-specific parameters for the shape of at least one of the patient's teeth and a parametric treatment prediction engine configured to identify an estimated and/or intended outcome of orthodontic treatment of a patient based on the 3D parametric arch model and historic models of a plurality of patients and/or idealized tooth arch models.

In some embodiments, the system includes a treatment projection rendering engine configured to render the 3D parametric arch model.

In some embodiments, the photo parameterization engine, the parametric treatment prediction engine, and the treatment projection rendering engine are together configured to perform the methods described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
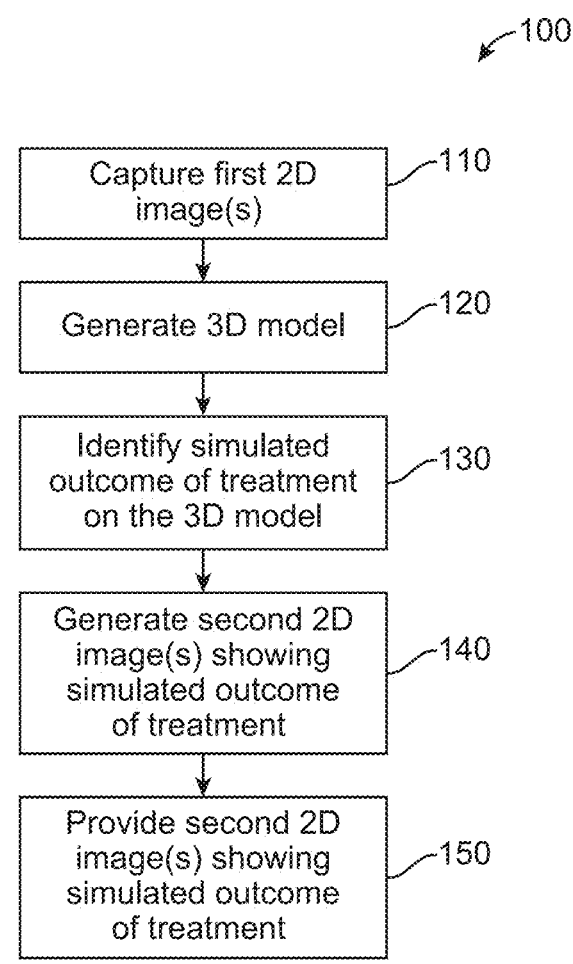
FIG. 1 illustrates a method of providing an estimated outcome of orthodontic treatment, in accordance with one or more embodiments herein.

The implementations discussed herein provide tools, such as automated agents, to visualize the effect of correcting malpositioned teeth/jaws, malocclusion, etc., without the computational burden(s) and/or expense(s) of scanning a patient's dentition or impressions of the dentition, and to calculate final positions of a treatment plan on a patient's dentition, etc. As discussed in detail herein, these techniques may involve obtaining a two-dimensional (2D) representation (such as an image) of a patient's dentition, obtaining one or more parameters to represent attributes of the patient's dentition in the 2D representation, and using the one or more parameters to compare the attributes of the patient's dentition with attributes of model arches, such as those of historical cases and/or those representing idealized arch forms. The techniques herein may provide a basis to simulate a simulated outcome of a dental treatment plan.

A "simulated outcome of a dental treatment plan," as used herein, may include an estimated and/or intended outcome of the dental treatment plan, such as after implementation of one or more dental procedures, such as orthodontic procedures, restorative procedures, etc. An "estimated outcome of a dental treatment plan," as used herein, may include an estimate of a state of a patient's dentition after dental procedures. An estimated outcome of a dental treatment plan, as used herein, may, in some instances, be different from an "actual outcome of a dental treatment plan," which may represent the state of a patient's dentition after implementation of the dental treatment plan. Estimated and actual outcomes of a dental treatment plan, as used herein, may, in various instances, be different from an "intended outcome of a dental treatment plan," which may represent the intended state of a patient's dentition after implementation of a dental treatment plan. It is further noted that an "estimated outcome of an orthodontic treatment plan" may include an estimate of a state of a patient's dentition after correction of any malpositioned teeth/jaws, malocclusion, etc., the patient suffers from. In some implementations, an estimated outcome of an orthodontic treatment plan includes the estimated state of the patient's dentition if the patient's dentition has been changed to have a model and/or ideal arch form, as reflected according to one or more databases of historical cases and/or idealized arch forms. An "actual outcome of an orthodontic treatment plan" may represent the state of a patient's dentition after implementation of the orthodontic treatment plan; an "intended outcome of an orthodontic treatment plan" may represent an intended state of a patient's dentition after implementation of an orthodontic treatment plan.

A better understanding of the features and advantages of the present disclosure will be obtained by reference to the following detailed description that sets forth illustrative embodiments, in which the principles of embodiments of the present disclosure are utilized, and the accompanying drawings.

FIG. 1 illustrates an example of a method 100 of providing an estimated and/or intended outcome of a dental treatment plan, in accordance with one or more embodiments herein. The method 100 may be executed by any of the systems disclosed herein. It is noted that various examples may include more or fewer blocks than those depicted in FIG. 1.

At block 110, one or more two-dimensional (2D or 2-D) image(s) of a patient are captured. In some embodiments, the 2D image(s) depict the mouth of the patient and include one or more images of the face, head, neck, shoulders, torso, or the entire patient. The 2D image(s) of the patient may include an image of the patient with the patient's mouth in one or more positions; for example, the patient's mouth may be a smiling position, such as a social smiling position, a repose position with relaxed muscles and lips slightly parted, or anterior retracted open bite or closed bite positions.

In some embodiments, the image of the patient is obtained with an image capture device. An "image capture device" (i.e., "image capture system") as used herein, may include any system capable of capturing an image. Examples of image captures devices include a camera, smartphone, digital imaging device, a component of a computer system configured to capture images, etc. The image may be captured with a lens at a predetermined focal length and at a distance from the patient. The image may be captured remotely and then received for processing. In some implementations, the image of the patient is obtained from a computer-storage device, a network location, a social media account, etc. The image may be a series of images or video captured from one or more perspectives. For example, the images may include one or more of a frontal facial image and a profile image, including one or more three-quarter profile images and full profile images.

At block 120, a three-dimensional (3D or 3-D) model of the patient's teeth is generated based on the 2D image of the patient. As discussed in more detail with respect to FIG. 6 and elsewhere herein, generating a 3D model may include identifying the patient's teeth. Generating a 3D model may further include identifying a patient's gums, lips, and/or mouth opening, forming a parametric model for each identified tooth, and combining the parametric teeth models into one or more (e.g., two, three, etc.) parametric arch models. The parametric models of the patient's teeth and arch may be based on or in reference to mean parametric tooth and arch models, as discussed further herein.

A "parametric model of a patient's teeth" (e.g., a "parametric model of a patient's dentition") as used herein, may include a model of a patient's dentition (e.g., a statistical model) characterized by a probability distribution with a finite number of parameters. A parametric model of a patient's dentition may include a parametric model of the patient's teeth and/or arch. A parametric model may comprise a model representing objects in various dimensions, and may include a parametric 2D model, a parametric 3D model, etc. Use of a parametric model of a patient's dentition to model the patient's teeth may reduce the memory and computational demands when manipulating, comparing, or otherwise using digital models, as descried herein and simplify comparisons between different models. In some implementations, a parametric model of a tooth can be expressed as:

$$S_\tau^C + \Sigma^{|B\tau|} \alpha_\tau^i B_\tau^i \qquad \text{eq. (1)},$$

where $S_\tau^C$ is a mean tooth shape, a generic parameter. Each tooth (for example, tooth number 6, the upper right canine in the universal tooth numbering system, has its own mean tooth shape) calculated from thousands of teeth with same tooth number, as discussed herein. The symbol T may represent the index for each tooth, which may be based on the universal tooth numbering system or another numbering system, $B_\tau^i$ may be the principal components of the shape of each tooth, also a generic parameter, and $a_\tau^i$ may be the coefficients for the principal components of the shape of the teeth, a case specific parameter. Accordingly, eq. (1) can be used to express a parametric model of each of a specific patient's teeth based on each tooth's particular shape relative to a mean tooth shape for that tooth (for example, a left lower incisor, right upper canine, etc.).

A parametric model of a patient's dentition can be expressed as:

$$Z_\tau = \Phi T T_\tau T_\tau^C (S_\tau^C + \Sigma_i^{|B\tau|} a_\tau^i B_\tau^i) \qquad \text{eq. (2)},$$

where $S_\tau^C + \Sigma_i^{|B\tau|} \alpha_\tau^i B_\tau^i$ is as discussed above with reference to eq. (1); $T_\tau^C$ is the mean tooth position, a generic parameter; $T_\tau$ is the deviation of the position of a patient's tooth from the corresponding mean tooth position, a case-specific parameter; and $\Phi$ is an arch scaling factor that scales the parametric, unit-less, values to real world values, also a case-specific parameter. T is the global perspective of the arch from a viewpoint and is a case-specific parameter and in some embodiments, is only used when matching to a 2D image, because arch scans typically do not have a perspective, whereas a 2D image, such as a camera, does.

Figure 2:
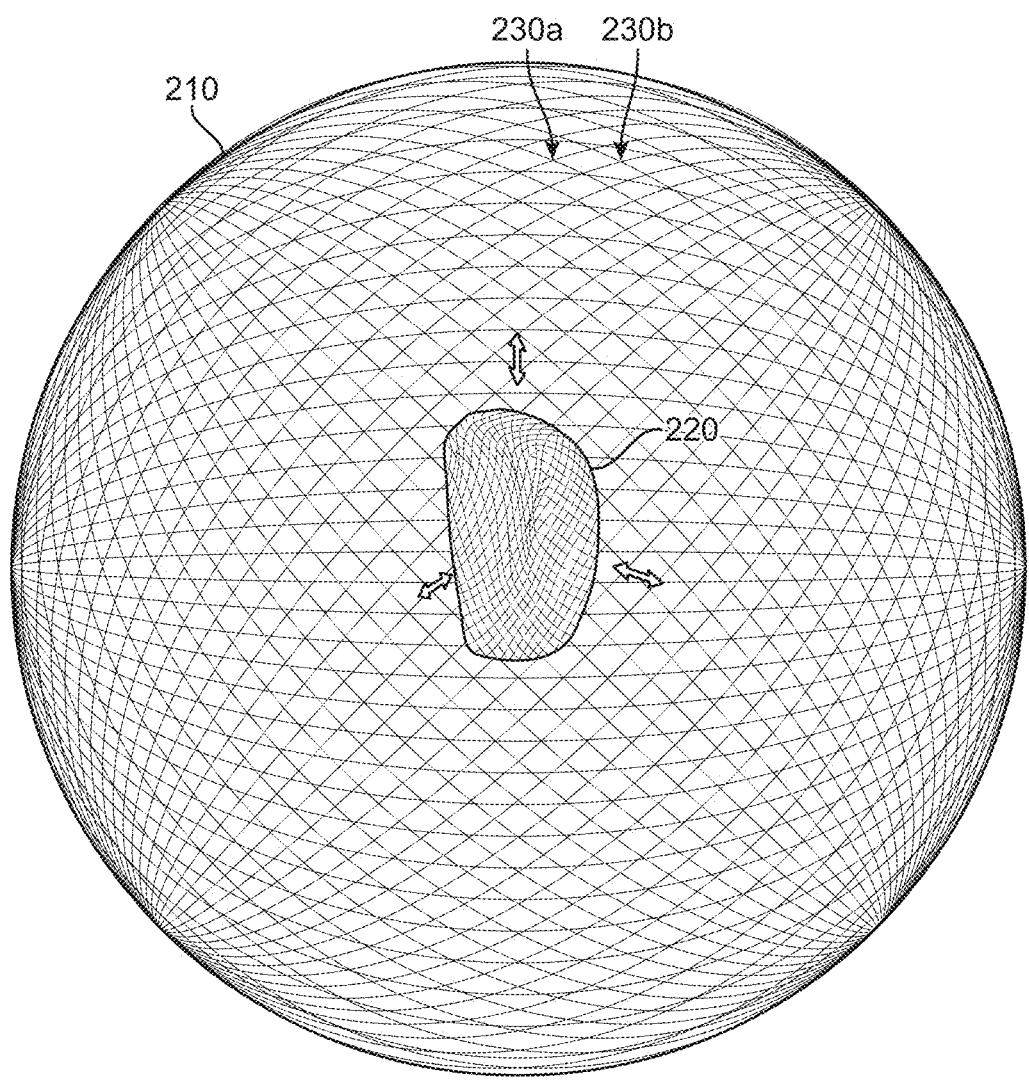
FIG. 2 illustrates a parametric tooth model, in accordance with one or more embodiments herein.
Figure 3A:
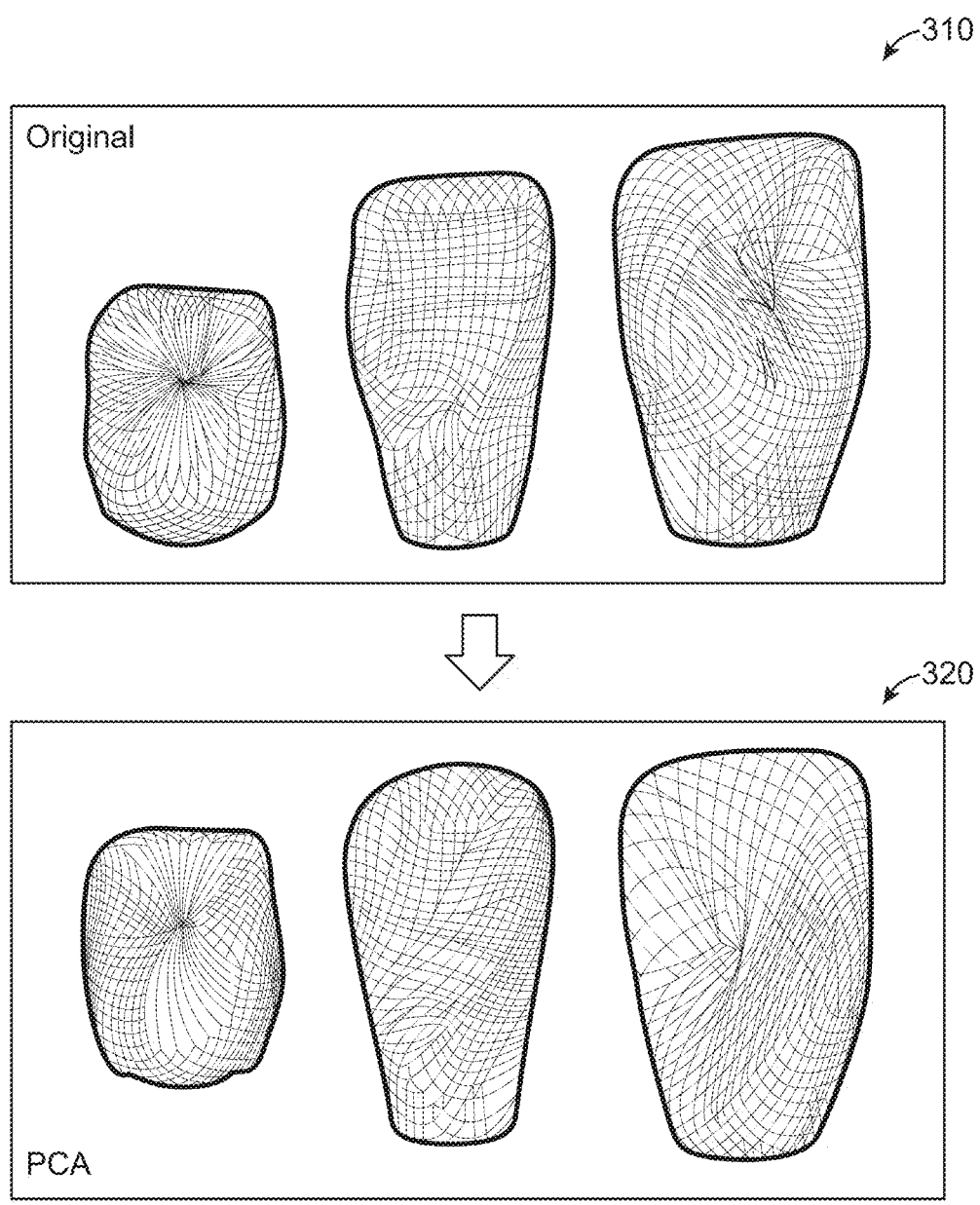
FIG. 3A illustrates an example of how well a parametric tooth model matches an original 3D model, in accordance with one or more embodiments herein.

To generate a parametric 3D model of a patient's tooth from a 3D tooth model derived from an image of a patient's tooth or from another method known in the art, the tooth may be modeled based on displacement of the scanned tooth surface from a fixed shape, such as a fixed sphere. To illustrate this point, reference is made to FIG. 2, illustrating a parametric tooth model, in accordance with one or more embodiments herein. In the example of FIG. 2, a sphere 210 having a plurality of vertices in fixed or known locations and orientations is shown. A tooth 220 may be placed or otherwise modeled at the center of the sphere 210. In some embodiments, the center of volume of the tooth 220, the scanned portion of the tooth 220, or the crown of the tooth 220, may be aligned with the center of the sphere 210. Then each vertex 230a, 230b of the sphere 210 may be mapped to a location on the surface of the tooth model. In some embodiments, the mapping may be represented by an n*3 matrix, where n represents the number of points on the sphere, such as 2500, and then for each point, the x, y, and z location is recorded. In some embodiments, the matrix stores the difference between a location on a mean tooth with the corresponding position on the model of the actual. In this way, each tooth is represented by the same 2500 points, and differences between the teeth are easily compared with each other. The difference may be represented using PCA components as $\Sigma_i^{|b\tau|} a_\tau^i B_\tau^i$, wherein each specific case eventually has a unique set of $a_\tau^i$, since $B_\tau^i$ is generic for all cases. To illustrate this point, reference is made to FIG. 3A, showing an example of how well parametric models 320 of the teeth match the original 3D models 310. The parameters of a particular tooth may be stored in a datastore, such as a database and may be represented by $a_\tau^i$.

A parametric model of a patient's arch may involve parameterizing the location and orientation of each tooth in an arch and the scale of the arch. The case-specific parameters for a particular tooth may be stored in a matrix or other datastore, as represented by eq. (3):

$$T_\tau = \begin{bmatrix} \xi_{00} & \xi_{01} & \xi_{02} & \Delta_{\tau,x} \\ \xi_{10} & \xi_{11} & \xi_{12} & \Delta_{\tau,y} \\ \xi_{20} & \xi_{21} & \xi_{22} & \Delta_{\tau,z} \\ 0 & 0 & 0 & 1 \end{bmatrix}; \qquad \text{eq. (3)}$$

where $\xi_{ij}$ are the rotational components that define the orientation of the tooth with respect to the arch and may be a function of $\alpha_\tau$, $\beta_\tau$, $\gamma_\tau$, the 3 rotation angles of the tooth. $\Delta_{\tau,x}$, $\Delta_{\tau,y}$, and $\Delta_{\tau,z}$ are the translation of the center point of the tooth with respect to the arch origin. The rotation may be based on the orientation of orthogonal axis of each tooth, for example, the long axis, the buccal-lingual axis, and the mesial-distal axis with respect to a fixed reference or with respect to a mean rotation. In some embodiments one or more of these components may be represented as deviations or changes relative to a mean arch, discussed herein.

Similarly, the scaling factor, $\Phi$ is applied to the teeth and the arch locations of the teeth to scale the arch from a generic or unit-less representation to a real world scale that represents the actual size and location of the teeth in the arch. In some embodiments, scaling may be between projected 3D units, for example, millimeter, to images size, for example, pixels.

As discussed above, and elsewhere herein, the parametric models of the arch, including the teeth, may be represented based on a mean arch model, including the teeth. The mean arch model may be determined based on an average of a large dataset of patient arch scans. In some embodiments, the mean arch model may be based on a large dataset of parameterized arches.

Figure 3B:
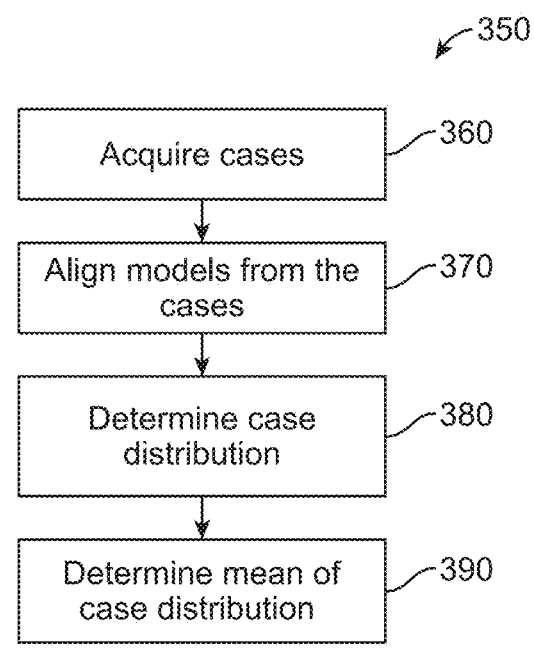
FIG. 3B illustrates a method of determining generic parameters from historic and/or idealized cases, in accordance with one or more embodiments herein.

For example, a mean arch may be built from a set of previously scanned and/or segmented arches. FIG. 3B depicts an example of a method 350 of determining a mean arch model and is discussed in detail further herein.

Figure 5:
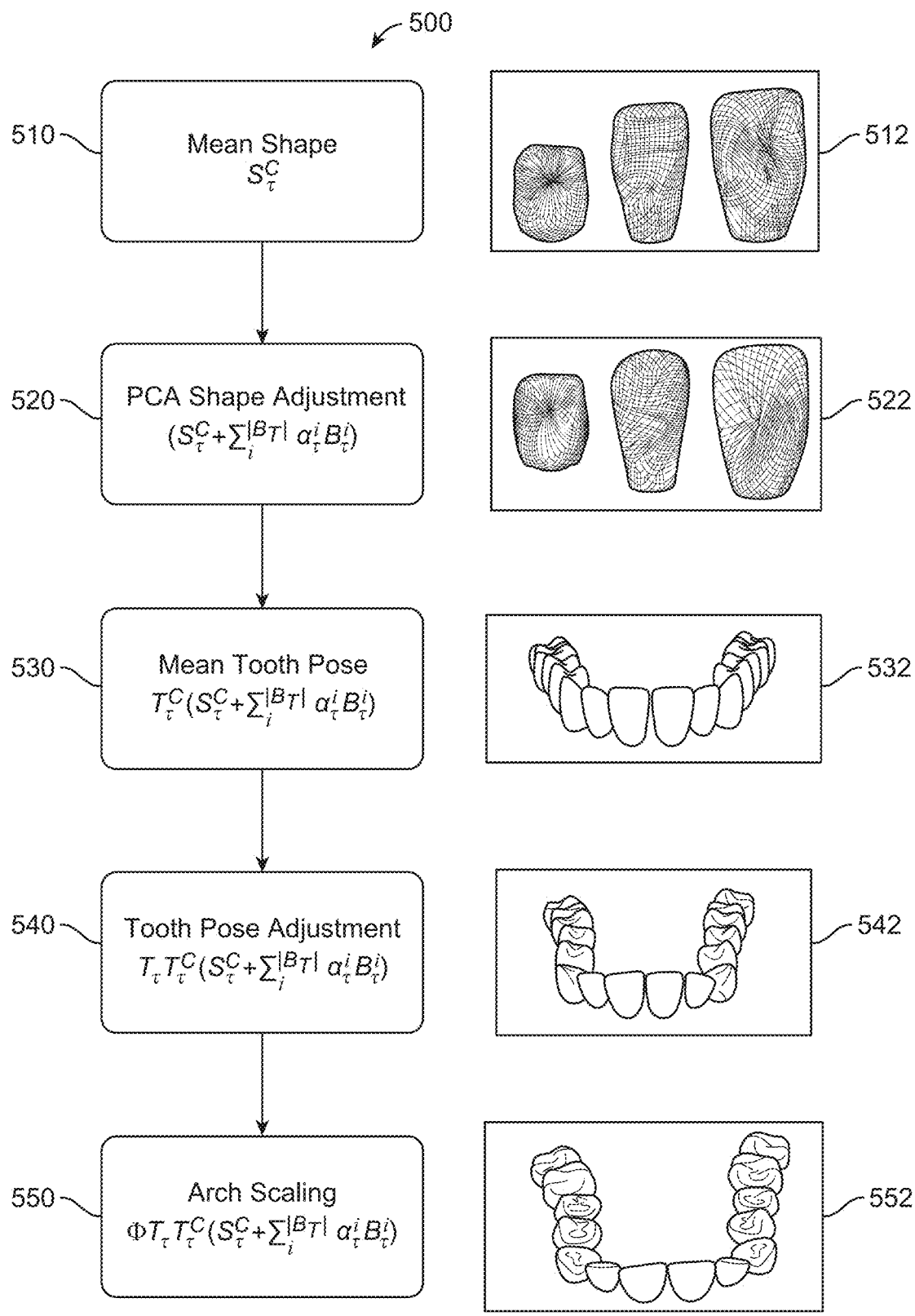
FIG. 5 depicts a method of generating a parametric model of a patient's teeth, and converting the parametric model into a 3D model of a dental arch, in accordance with one or more embodiments herein.

In some implementations, a parametric model of an arch may be converted into a 3D model of the arch. FIG. 5 depicts a method 500 of converting a parametric model of one or more teeth into a 3D model of a dental arch, according to some implementations, and is discussed in detail further herein.

Returning to FIG. 1, at block 130, an estimated and/or intended outcome of a dental treatment plan on the 3D model is identified to obtain an estimated and/or intended outcome of the orthodontic treatment plan. The estimated and/or intended outcome of a dental treatment plan may be based on a parametric model of the patient's teeth at positions indicated based on a predetermined arch model, as discussed with respect to FIGS. 9-11. In some embodiments, a predetermined arch model may be based on a mean arch model may be based on a historic mean of collected arch scans or other arch models from patients. In some embodiments, the predetermined arch model may be an idealized model, for example, based on a clinically ideal arch or an arch model wherein tooth positions and/or orientations are determined in advance, such as based on one or more of their aesthetic and clinical properties, such as proper occlusion. In some embodiments, an estimated and/or intended outcome of the dental treatment plan may correspond to an intended final position (or estimate thereof) of the patient's teeth after implementation of the treatment plan. In some embodiments, the estimated and/or intended outcome of dental treatment may correspond to estimates of final and intermediate positions during the course of the treatment plan. As noted herein, the dental treatment plan may comprise an orthodontic treatment plan, a restorative treatment plan, some combination thereof, etc.

At block 140, second 2D image(s) are generated showing the estimated and/or intended outcome of orthodontic treatment. The image(s) may be a 2D facial image of the patient with teeth aligned according the estimated and/or intended outcome of the dental treatment plan as discussed herein. In some embodiments, the image may include an estimated and/or projected texture of the patient's teeth, for example as discussed below, with respect to FIG. 9 and elsewhere herein. A "projected texture" or "estimated texture" of a patient's teeth, as used herein, may include a projection/estimation of texture of teeth and may include the feel, appearance, consistency, and/or other attributes of the surface of the teeth. At block 150, the second 2D image(s) generated at block 140 are provided to a user. For example, the image may be rendered for viewing by a patient or dental professional. In some embodiments, the second 2D image may be loaded into memory or retrieved from memory.

Turning to FIG. 3B, FIG. 3B illustrates a method of determining generic parameters from historic and/or idealized cases, in accordance with one or more embodiments herein. At block 360, historic and/or idealized cases are acquired. The historic and/or idealized cases may be retrieved from a datastore. The historic and/or idealized cases may include cases representing previously scanned and segmented arch models. In some implementations, the historic and/or idealized cases may represent arch models of treated patients (e.g., of patients who in the past have undergone treatment) and/or idealized arch models representing intended outcomes of various forms of orthodontic treatment. In various implementations, the historic and/or idealized cases may represent arch models with idealized arch forms. In some implementations, the historic and/or idealized cases may include regions where model arches have teeth that correspond to a location of an implant to be inserted into the arch of a patient.

Figure 4:
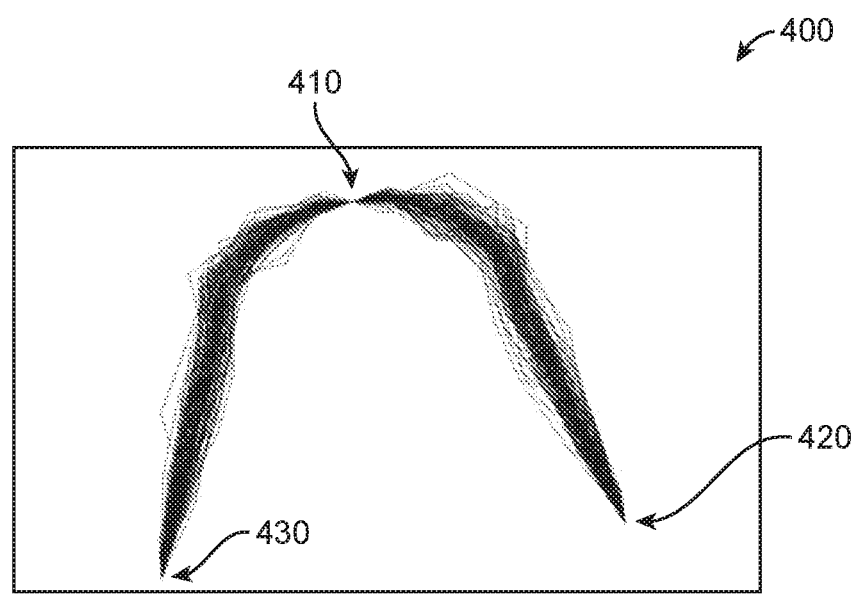
FIG. 4 illustrates the alignment of past cases for use in determining parameters of a parametric model, in accordance with one or more embodiments herein.

At block 370 the historic and/or idealized cases are aligned. In some implementations, each arch of the historical and/or idealized cases is aligned at a plurality of locations. As an example, each arch of the historical and/or idealized cases may be aligned at the following three locations: between the central incisors and at each distal end of the left and right side of each arch. For example, FIG. 4 shows a set of arches 400 aligned at location between the central incisors 410, at the left distal end of the arch 430, and the right distal end of the arch 420. It is noted the historic and/or idealized cases may be aligned at a variety of locations and a variety of numbers of locations without departing from the scope and substance of the inventive concepts described herein.

Returning to FIG. 3B, determining a mean arch model and determining arch model distributions may include performing sub operations at block 370. For example, each arch is averaged to determine $T_\tau^C$, then the individual tooth local tranformations are determined and compared to $T_\tau^C$ to determine $T_\tau$, then after aligning each tooth $\beta_\tau$ may be determined.

At block 380, the distribution estimation for case specific parameters are determined. For example, each tooth's relative shape, location, and rotation are determined in order to build a distribution for each case specific parameter. For example the distribution of the $a_\tau^i$, the coefficients for the principal components for the surface model of the each respective tooth in all of the retrieved models, is determined.

The location and orientation of each tooth may be averaged to determine a mean location for each tooth and the orientation of each tooth is averaged to determine a mean orientation for each tooth. The mean location and orientation are used to determine $T_\tau^C$.

At block 390, the mean of the distribution of the estimation for case-specific parameters is used as the generic parameters of mean tooth position and mean tooth shape.

FIG. 5 depicts a method 500 of generating a parametric model of one or more of a patient's teeth and converting the parametric model of one or more teeth into a 3D model of a dental arch, according to some implementations. The method 500 may be used for generating a 3D model of a tooth arch of a patient based on a parametric model of the patient's teeth.

At block 510, a mean shape of each tooth is determined. As an example, the mean shape, $S_\tau^C$, of each tooth is determined. In some embodiments, the mean shape may be based on the mean shape of a set of arches from historical and/or idealized cases, as discussed herein. In some embodiments, the mean shape may be rendered, for example, on a screen for viewing by a patient or dental professional. For example, mean tooth shapes 512 are rendered for viewing. In some embodiments, the mean shape may be loaded into memory or retrieved from memory. The mean shape may also be initialized as a set of matrices, one for each tooth.

At block 520, a principal component analysis shape adjustment is performed on the mean shape of the teeth. This adjustment adjusts the shape of the teeth based on the patient's particular teeth, for example, based on a scan of the patient's teeth, a 2D image, or other imaging technologies, as discussed herein. As an example, a principal component analysis shape adjustment is performed on the mean shape of the teeth, $S_\tau^C$. For each tooth in the model, the case-specific coefficients for the principal components, $a_\tau^i$, are applied to the principal component, $B_\tau^i$. After the shape adjustment is completed, in some embodiments, the adjusted shape may be rendered, for example, on a screen for viewing by a patient or dental professional. For example, adjusted tooth shapes 522 are rendered for viewing. In some embodiments, the adjusted shape may be stored into memory. The adjusted shape may also be stored as a set of matrices, one for each tooth.

At block 530, a mean tooth pose is determined. In some embodiments, the mean tooth pose may be based on the mean tooth pose of a set of arches from historical and/or idealized case, as discussed herein. In some embodiments, at block 530, each adjusted tooth 522 is placed in its corresponding mean location and orientation, as determined by the mean arch. In some embodiments, the mean tooth pose may be rendered, for example, on a screen for viewing by a patient or dental professional. For example, mean tooth pose 532 is rendered for viewing. In some embodiments, the mean tooth pose may be loaded into memory or retrieved from memory. The mean tooth pose may also be initialized as a set of matrices, one for each tooth in the tooth pose. In some embodiments, the mean tooth shapes from block 510 may be placed in their corresponding mean tooth pose at block 530 before the shapes of the teeth are adjusted at block 520. In other words, the order of block 520 and block 530 may be swapped.

At block 540, a tooth pose adjustment is performed on the mean tooth pose. This adjustment adjusts the shape of the teeth based on the patient's particular teeth, for example, based on a scan of the patient's teeth, a 2D image, or other imaging technologies as discussed herein. In some embodiments, the pose adjustment $T_\tau$ is based on the particular tooth pose of a patient's arches, as discussed above. In some embodiments, at block 540, the position and orientation of each tooth 522 is adjusted such that it is placed in a location and orientation as determined by the location and orientation of the teeth in a patient's imaged arch, or otherwise, as discussed herein. In some embodiments, the adjusted tooth pose may be rendered, for example, on a screen for viewing by a patient or dental professional. For example, adjusted tooth pose 542 is rendered for viewing. In some embodiments, the adjusted tooth pose may be stored in memory. The adjusted tooth pose may also be stored as a set of matrices and/or data structures, e.g., one for each tooth in the tooth pose. In some embodiments, the mean tooth shapes from block 510 may be placed in their corresponding adjusted tooth pose at block 540 before the shapes of the teeth are adjusted at block 520. In other words, the order of block 520 and blocks 530 and 540 may be swapped such that block 520 takes place after blocks 530 and 540.

At block 550, the arch is scaled such that it is generated according to the patient's tooth and arch size. In some embodiments, the arch scaling factor $\Phi$ is based on the particular tooth and arch of a particular patient, as discussed above. In various embodiments, the arch scaling factor may also be based on one or more of the image size of the 2D image of the patient, for example, when scaling the 3D model for integration into a 2D image In some embodiments, at block 550, the size of each tooth 522 and the arch is adjusted such that the scaled arch matches the size of a patient's arch, as determined, for example, by size of the teeth and arch in the patient's imaged arch, or otherwise, as discussed herein. In some embodiments, the scaled arch may be rendered, for example, on a screen for viewing by a patient or dental professional. For example, scaled arch 552 is rendered for viewing. In some embodiments, the scaled arch may be stored in memory. The scaled arch may also be stored as a set of matrices and/or data structures, one for each tooth in the tooth pose. In some embodiments, the mean tooth shapes from block 510 may be placed in their corresponding scaled position and size at block 550 before the shapes of the teeth are adjusted at block 520. In other words, the order of block 520 and blocks 530, 540, and 550 may be swapped such that block 520 takes place after blocks 530, 540, and 550.

The blocks of method 500 may be carried out in orders other than those shown in FIG. 5. For example, blocks 510 and 530 may be performed before blocks 520, 540, and 550. In some embodiments, blocks 510, 520, 530, and 550 may be carried out before block 540. These and other modifications to the order of the blocks in method 500 may be carried out without deviating from the spirit of the disclosure.

Figure 6:
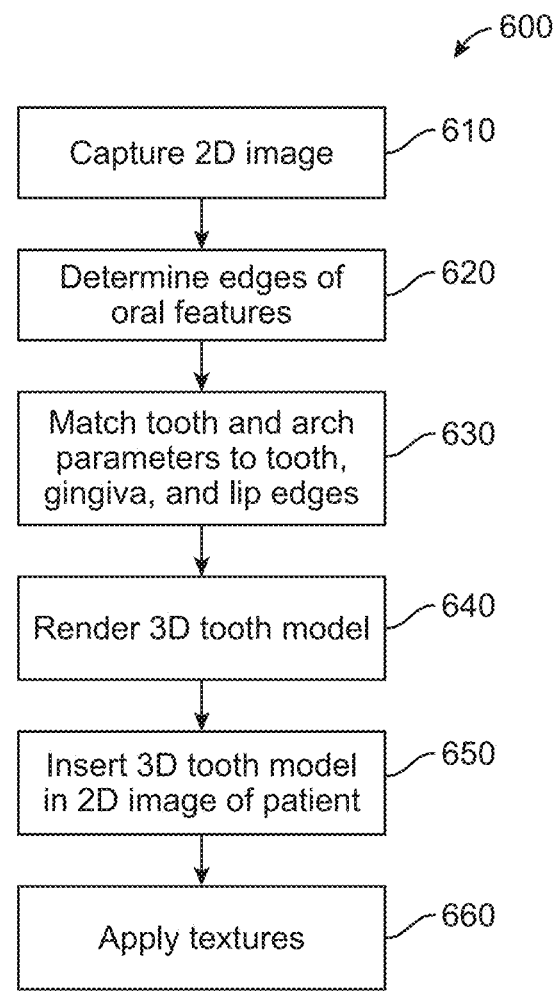
FIG. 6 depicts a method for constructing a 3D model from a 2D image, in accordance with one or more embodiments herein.

With attention to FIG. 6, FIG. 6 illustrates a method 600 for constructing a 3D model from a 2D image, according to one or more embodiments disclosed herein.

At block 610, a 2D image of a patient is captured. In some embodiments, the 2D image includes the mouth of the patient and one or more images of the face, head, neck, shoulders, torso, or the entire patient. The 2D image of the patient may include an image of the patient with their mouth in one or more positions. For example, the patient's mouth may be a smiling position, such as a social smiling position, a repose position with relaxed muscles and lips slightly parted, or anterior retracted open bite or closed bite positions.

In some embodiments the image of the patient is taken with an image capture system. The image may be captured with a lens at a predetermined focal length and at a distance from the patient. The image may be captured remotely and then received for processing. The image may be gathered from a storage system, a networked location, a social media website, etc. The image may be a series of images of video captured from one or more perspectives. For example, the images may include one or more of a frontal facial image and a profile image, including one or more three-quarter profile images and full profile images.

At block 620, edges of oral features of the patient are determined. For example, the edges of one or more of the patient's teeth, lips, and gingiva may be determined. An initial determination of the patient's lips (for example, the inner edges of the lips that define the mount opening), teeth, and gingiva contours may be identified by a machine learning algorithm, such as a convoluted neural network. The machine learning algorithm may be trained based on pre-identified labels of the lips, teeth, and gingiva visible within a 2D image of a patient. The initial contours may be weighted contours such that the machine learning algorithm's confidence that a given position in the image, such as at each pixel, is an edge or contour of a patient's lips, teeth, or gingiva.

The initial contours may be extracted from the image. The initial contours may have a brightness or other scale applied to them. For example, in a grey scale image of the contours, each pixel may be assigned a value between 0 and 255, which may indicate a confidence that the pixel is a contour or may indicate the magnitude of the contour at that location.

The pixels that denote the contours may then undergo binarization to change the pixels from a scale of, for example, 0 to 255, to a binary scale of, for example, 0 or 1, creating binarized tooth contours. In the binarization process, the value of each pixel is compared to a threshold value. If the value of the pixel is greater than the threshold, then it may be assigned a new first value, such as a value of 1 and if the pixel is less than the threshold, then it may be assigned a new second value, such as a value of 0, for example.

The binarized tooth contours may be thinned, whereby the contour's thickness is reduced to, for example, a single pixel in width, forming a thinned contour. The width of a contour for thinning may be measured as the shortest distance from a contour pixel adjacent to a non-contour pixel on a first side of a contour, to a contour pixel adjacent a non-contour pixel on a second side of the contour. The single pixel representing the thinned contour at a particular location may be located at the midpoint of the width between the pixel at the first side and the pixel at the second side. After thinning the binarized tooth contours, the thinned contour may be a single width contour at a location that corresponds to a midpoint of the binarized contour.

Figure 7A:
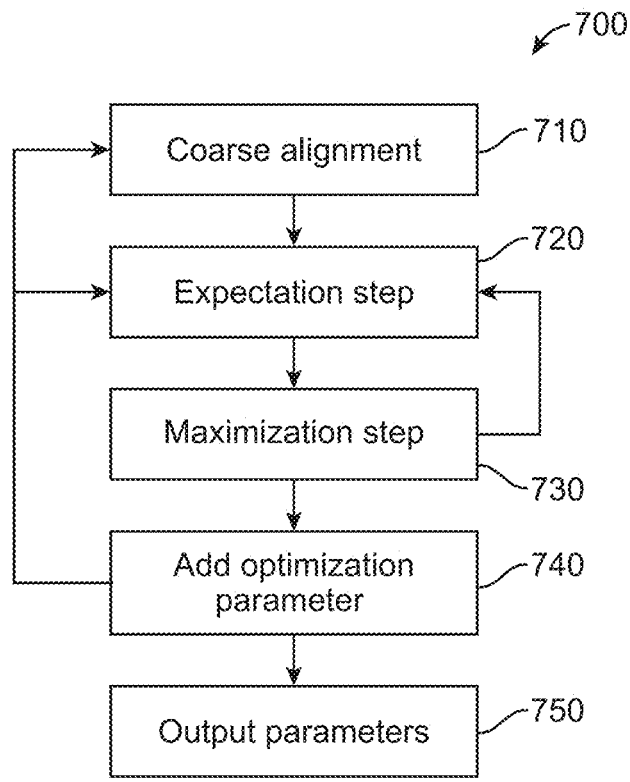
FIG. 7A depicts a method of building a patient-specific parametric model of a patient's teeth, in accordance with one or more embodiments herein.

At block 630, parameterized 3D tooth and arch models are matched to each of the patient's teeth that are depicted in the 2D image of the patient. The matching may be based on the edges, also referred to as contours, determined at block 630. FIG. 7A shows an example of a process of matching tooth and arch models to the edges. Returning to FIG. 6, after identifying and modeling the teeth and arch, or as part of such a process, missing or broken teeth may be inserted into the parameterized 3D tooth and arch model. For example, when a tooth is missing or significantly damaged, the parameterized model of that tooth may be replaced with a mean tooth model, thereby simulating a prosthetic tooth, such as a veneer, crown, or implant prosthetic. In some embodiments, the missing tooth may be left as a space in the arch. In some embodiments a broken tooth may be left, as is, without replacing it with a mean shape tooth.

During the matching process, the case specific parameters of a parametric arch model are varied and iterated through until a match between the parametric arch model and the teeth depicted in the 2D image is found. This match may be determined based on a projection of the edges of a silhouette of the parametric model match with the edges of the lips, teeth, and gingiva identified in the 2D image.

At block 640, the parametric model of the patient's teeth is rendered. An example of a process of rendering a parametric model of teeth is described with respect to FIG. 8, and elsewhere herein. During the rendering process, a 3D model of the patient's teeth is formed based on data describing the teeth and arch of the patient. For example, based on the parametric 3D model formed at block 630, or otherwise describe herein. In some embodiments, the 3D model is directly inserted into the 2D image of the patient. In such embodiments, the actions in block 640 may be omitted or merged with the actions of block 650 such that, for example, the 3D tooth model is rendered in 2D form for insertion into the 2D image.

Optionally, at block 640, simulated treatments or viewing customizations, such as gingiva line adjustment, jaw position adjustment, missing tooth insertion, or broken tooth repair, can be applied to the 3D model before rendering into 2D form. In some embodiments, the edges of the parametric model (for example, lips, gingiva line, missing or broken teeth) may be altered to display simulated results of cosmetic or other treatments and procedures or to adjust the 2D patient image for customized viewing. For example, a user, such as a dental professional or patient, may adjust the gingiva line to simulate gum treatments. As another example, the user may opt to show, hide, or repair missing or chipped teeth to simulate tooth repair or replacement procedures. In another example, the user may opt to adjust jaw position in the pre- or post-treatment simulated image to simulate appearances with the jaw open, closed, or partially open. A jaw position parameter can be defined by a distance between a tooth surface in the upper jaw and a tooth surface in the lower jaw, such as the distance between the incisal surface of the upper central incisor in relation to the incisal surface of the lower central incisor. The jaw position parameter can be defined and varied by the user. For example, the distance between the incisal surface of the upper central incisor and the incisal surface of the lower central incisor may be varied between −5 mm (indicating, the lower incisors overlapping with the upper incisors by 5 mm) and 10 mm (indicating, a gap of 10 mm between the upper incisors and the lower incisors). The gingiva line can be adjusted by replacing the patient gingiva line mask shape with the mean gingiva line mask shape from the historic shape datastore. Display of gingiva line adjustment can be optionally selected or adjusted by the user. Missing or broken teeth can be replaced with a mean tooth shape from the historic shape datastore. Display of missing tooth replacement or broken tooth repair can be optionally selected by the user. Simulated treatments or viewing customizations may be rendered, for example, on a screen for viewing by a user, patient, or dental professional.

At block 650, the 3D tooth model is inserted into the 2D image of the patient. The inner lip edges determined at block 620 may be used to define the outline of the patient's mouth in the 2D image. At block 650, the area of the 2D image defined by the mouth opening may be removed and the 3D model may be placed behind the 2D image and within the mouth opening.

At block 660, textures are applied to the teeth. An example of applying textures is discussed in more detail with respect to FIG. 9. In some implementations, when applying textures to the teeth, the 2D image of the patient is projected onto a 3D model of the teeth, such as the parametric 3D model of the patient's teeth determined, for example, at block 630. When projecting the 2D image into the 3D model, the pixels at each location in the 2D image are assigned to a location on the 3D model. In some embodiments, the pixel value or texture information from 2D image is processed before being applied to 3D model. Other techniques, such as inpainting, blurring, image processing filters, pix2pix transformation technologies, etc., can also be used to generate textures for application to the surfaces of the 3D model. The projected pixels at each location on a surface of the 3D model form a texture for that model. For example, the pixels projected onto a particular tooth of the patient form a texture for that tooth model. This texture can be applied to the 3D tooth model.

FIG. 7A depicts a method 700 of building a patient-specific parametric model of a patient's teeth according to some embodiments.

At block 710, a course alignment of each corresponding mean parametric tooth is aligned with a respective center of a tooth in the 2D image. A center of the parametric tooth may be determined based on the area center of a projection of the parametric tooth's silhouette. A center of a tooth identified in the 2D image of the patient may be determined based on an area center of an area defined by tooth edges and a corresponding lip and/or gingiva edge. The respective centers of the 2D image tooth and the parametric tooth may be aligned before the expectation step and maximization steps of blocks 720 and 730, respectively.

The method 700 may dynamically generate the parametric tooth models with lip and gingiva edges for matching with the teeth in the 2D image and block 710. In addition or alternatively, the lip and gingiva edges maybe applied and/or dynamically adjusted at any of blocks 720, 730, and 740. The 3D tooth models may be computed on the fly for varying lip and gingiva line placement. Using such models provides for a much more accurate parametric model than using gingiva lines alone.

Figure 7B:
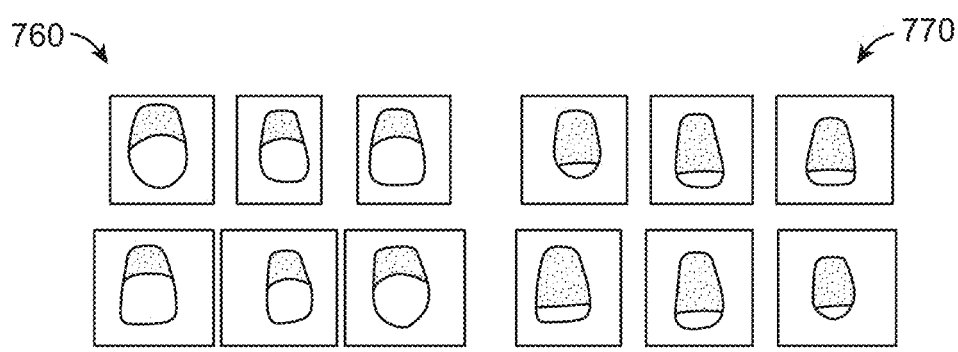
FIG. 7B depicts tooth models with gingiva and lip edges, in accordance with one or more embodiments herein.

When lip and gingiva information is applied at block 710, in some embodiments, only the portion of the parametric model beyond the lip and/or gingiva edges is used to determine the area center of the tooth. Turning to FIG. 7B, the figure depicts examples of tooth models with gingiva edges 760 and tooth models with lip edges 770. At any of blocks 710, 720, 730, 740, the location of the gingiva and/or lip edges may be modified to adjust the fit of the silhouette of the tooth with the visible portion of a corresponding tooth in the 2D image.

The addition of the lip or gingiva edges of the teeth significantly improve the efficiency and operation of process. The result is that the process much more realistically matches teeth models to the 2D image and the process works with a much wider variety of photos, as compared to a process that does not apply lip and gingiva edges to teeth models.

Returning to FIG. 7A, at block 720, an expectation step is performed. In some implementations, an Expectation Management (EM) engine and/or an engine configured to create a 3D model performs block 720. At the expectation step, a silhouette of the tooth is projected onto the 2D image and the edges of the silhouette are evaluated against the edges of the tooth in the 2D image as determined based on the lip, gingiva, and tooth edges. The evaluation may be a determination of the normal at a location at the edge of the silhouette and the closest location in the 2D image with a similar normal. Then the probability that the two edges are the same is determined. This process may be repeated for each location at the edge of the silhouette.

At block 730, a maximization step of the EM engine is performed. At the maximization step a small angle approximation is used in order to provide for an analytical solution to the maximization. The small angle approximation and analytical solution provides a much improved solution as compared to other methods, such as the Gaussian-Newton iterative method. The small angle approximation significantly reduces computation time and resolves to an accurate solution much faster.

Blocks 720 and 730 may be performed iteratively on a single parameter or subset of parameters, performing the expectation step then the maximization step, then back to the expectation step and so on until a threshold of convergence for the single parameter or subset of parameters is reached. Then the process may proceed to block 740.

At block 740, an optimization parameter or subset of parameters are added to the parametric model. For example, optimization of the parametric model may begin with $\Phi$ and T, then after iterating through the EM blocks 720 and 730, additional parameters are added. For example, $T_\tau$ may be added and then optimized through the EM blocks 720 and 730 for additional iterations. The number of iterations before adding additional parameters may vary. In some embodiments, the EM blocks 720 and 730 may be iterated through 3, 5, 7, 10, 15, 20, or an arbitrary number (e.g., any integer) of times. Finally, $a_\tau^i$ may be added to the parametric model, which is processed though the EM blocks 720 and 730 until convergence is reached. During this process, outliers may be determined and filtered out. In some embodiments, after block 740, rather than looping back to block 720 and proceeding directly to the expectation step, the process 700 may loop back to block 710, where a coarse alignment procession is performed based on the updated parametric model.

At block 750 the parameters of a parametric model are output to another engine or even to a datastore for later retrieval. For example, a rendering engine may retrieve the parameters for the parametric model for rendering, as described with respect to FIG. 8, and elsewhere herein.

Figure 8:
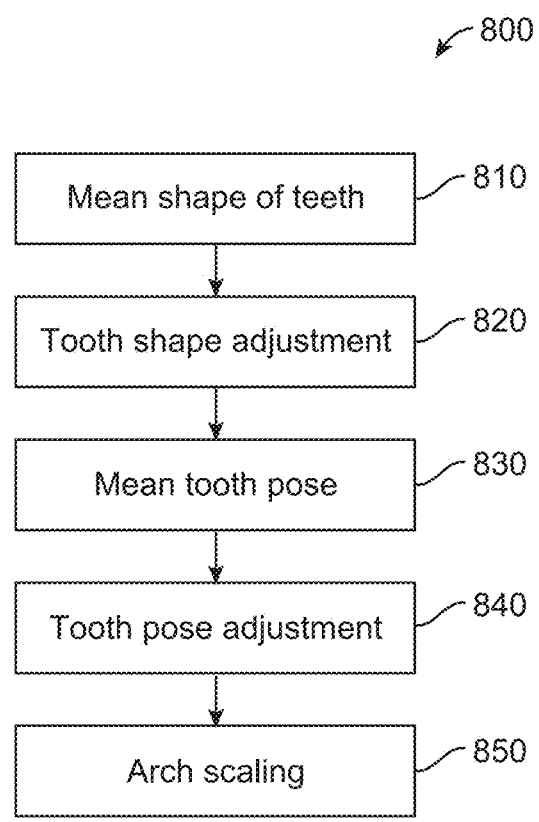
FIG. 8 depicts a method of rendering patient's teeth in an initial position using a parametric model of the patient's arch, in accordance with one or more embodiments herein.

FIG. 8 depicts a method 800 of rendering patient's teeth in an initial position, using a parametric model of the patient's arch, in accordance with one or more embodiments herein.

At block 810, the mean shape, $S_\tau^C$, of each tooth is determined. In some embodiments, the mean shape may be based on the mean shape of a set of arches taken, e.g., from historical cases and/or those representing idealized arch forms, as discussed herein. In some embodiments, the mean shape may be rendered, for example, on a screen for viewing by a patient or dental professional. In some embodiments, the mean shape may be loaded into memory or retrieved from memory. The mean shape may also be initialized as a set of matrices, one for each tooth.

At block 820, a principal component analysis shape adjustment is performed on the mean shape of the teeth, S. For each tooth in the model, the case specific coefficients for the principal components, $a_\tau^i$, are applied to the principal component, $B_\tau^i$. After the shape adjustment is completed, in some embodiments, the adjusted shape may be rendered, for example, on a screen for viewing by a patient or dental professional. For example, adjusted tooth shapes are rendered for viewing. In some embodiments, the adjusted shape may be stored into memory. The adjusted shape may also be stored as a set of matrices, one for each tooth.

At block 830, the mean tooth pose is determined. In some embodiments, the mean tooth pose may be based on the mean tooth pose of a set of scanned arches, as discussed herein. In some embodiments, at block 830, each adjusted tooth is placed in its corresponding mean location and orientation, as determined by the mean arch. In some embodiments, the mean tooth pose may be rendered, for example, on a screen for viewing by a patient or dental professional. In some embodiments, the mean tooth pose may be loaded into memory or retrieved from memory. The mean tooth pose may also be initialized as a set of matrices and/or other data structures, e.g., one for each tooth in the tooth pose. In some embodiments, the mean tooth shapes from block 810 may be placed in their corresponding mean tooth pose at block 830 before the shapes of the teeth are adjusted at block 820. In other words, the order of block 820 and block 830 may be swapped.

At block 840, a tooth pose adjustment is performed on the mean tooth pose. In some embodiments, the pose adjustment $T_\tau$ is based on the particular tooth pose of a patient's arches, as discussed above. In some embodiments, at block 840, the position and orientation of each tooth is adjusted such that it is placed in a location and orientation as determined by the location and orientation of the teeth in patient's arch, or otherwise, as discussed herein. In some embodiments, the adjusted tooth pose may be rendered, for example, on a screen for viewing by a patient or dental professional. In some embodiments, the adjusted tooth pose may be stored in memory. The adjusted tooth pose may also be stored as a set of matrices and/or other data structures, e.g., one for each tooth in the tooth pose. In some embodiments, the mean tooth shapes from block 810 may be placed in their corresponding adjusted tooth pose at block 840 before the shapes of the teeth are adjusted at block 820. In other words, the order of block 820 and blocks 830 and 840 may be swapped such that block 820 takes place after blocks 830 and 840.

At block 850, the arch is scaled such that it is generated with tooth dimensions according to the patient's tooth and arch size. In some embodiments, an arch scaling factor $\Phi$ is based on the particular tooth and arch of a particular patient, as discussed above. In some embodiments, at block 850, the size of the arch is adjusted such that the scaled arch matches the size of a patient's arch, as determined, for example, by size of the teeth and arch in the patient's arch, or otherwise, as discussed herein. In some embodiments, the scaled arch may be rendered, for example, on a screen for viewing by a patient or dental professional. In some embodiments, the scaled arch may be stored in memory. The scaled arch may also be stored as a set of matrices and/or data structures, e.g., one for each tooth in the tooth pose. In some embodiments, the mean tooth shapes from block 810 may be placed in their corresponding scaled position and size at block 850 before the shapes of the teeth are adjusted at block 820. In other words, the order of block 820 and blocks 830, 840, and 850 may be swapped such that block 820 takes place after blocks 830, 840, and 850.

The blocks of the method 800 may be carried out in orders other than those shown in FIG. 8. For example, blocks 810 and 830 may be performed before blocks 820, 840, and 850. In some embodiments, blocks 810, 820, 830, and 850 may be carried out before block 840. These and other modifications to the order of the blocks in method 800 may be carried out without deviating from the spirit of the disclosure.

Figure 9:
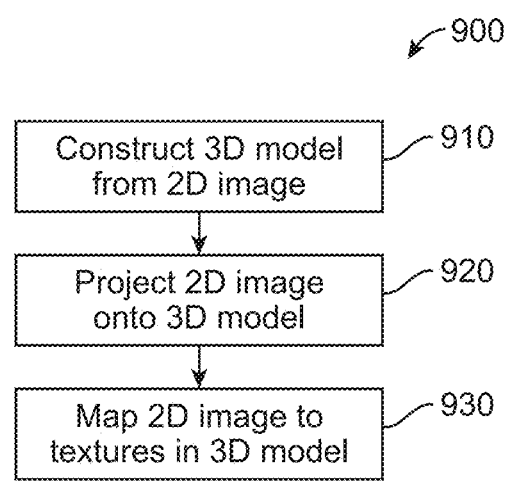
FIG. 9 depicts a method of constructing and applying textures to a 3D model, in accordance with one or more embodiments herein.

FIG. 9 depicts a method 900 of constructing and applying textures to a 3D model, in accordance with one or more embodiments herein. Textures may aid in providing detail, such as color information, to the 3D model of a patient's teeth. As described herein, the process 900 uses images of the patient's teeth to provide lifelike textures for a patient's teeth.

Accordingly, at block 910, a 3D model of the patient's teeth and a 2D image of the patient are acquired, as described elsewhere herein, for example, in the discussion related to FIG. 5. The 2D image and the 3D model should depict the teeth in the same positions, for example, the 3D model could be a parametric model derived from the 2D image of the patient.

At block 920, the 2D image of the patient's teeth is projected onto the 3D model and the image is aligned with the model. Such alignment may be carried out by matching contours in the 3D model with contours in the 2D image. Contours may include lip, gingiva, and teeth edges, determined as described elsewhere herein.

At block 930, the color information from the 2D image is mapped as textures to the 3D model. Color information may include lighting conditions, such as specular highlights, accurate tooth coloration and textures, and other tooth features, such as tooth jewelry, gold teeth, etc. Once the textures are mapped to the 3D model, the teeth in the 3D model may be repositioned, for example to depict an estimated and/or intended outcome of a dental treatment plan (e.g., an orthodontic treatment plan, a restorative treatment plan, some combination, thereof, etc.). Such a final position includes both accurate color and tooth feature information and accurate 3D positioning of the patient's teeth and may be used for example, in simulating an estimated and/or intended outcome of a dental treatment plan (e.g., a final orthodontic position) of a patient's teeth, as described with respect to FIG. 10A, FIG. 10B, and/or elsewhere herein.

In some embodiments, the textures model is adjusted to simulate clinical or beautification treatments. For example, color may be adjusted to simulate tooth whitening procedures. Simulating such treatments may include generating a mask from a 2D projection of the 3D tooth model with the model in an arrangement for insertion in the 2D image, for example, in either the initial or final positions. The mask can be applied to the 2D image of the patient's teeth in either the initial or final positions. Color adjustment or whitening can be further applied to the mask region. Color adjustment and whitening parameters can be optionally selected and adjusted by the user. Color adjustments and whitening may be rendered, for example, on a screen for viewing by a user, patient, or dental professional.

Figure 10A:
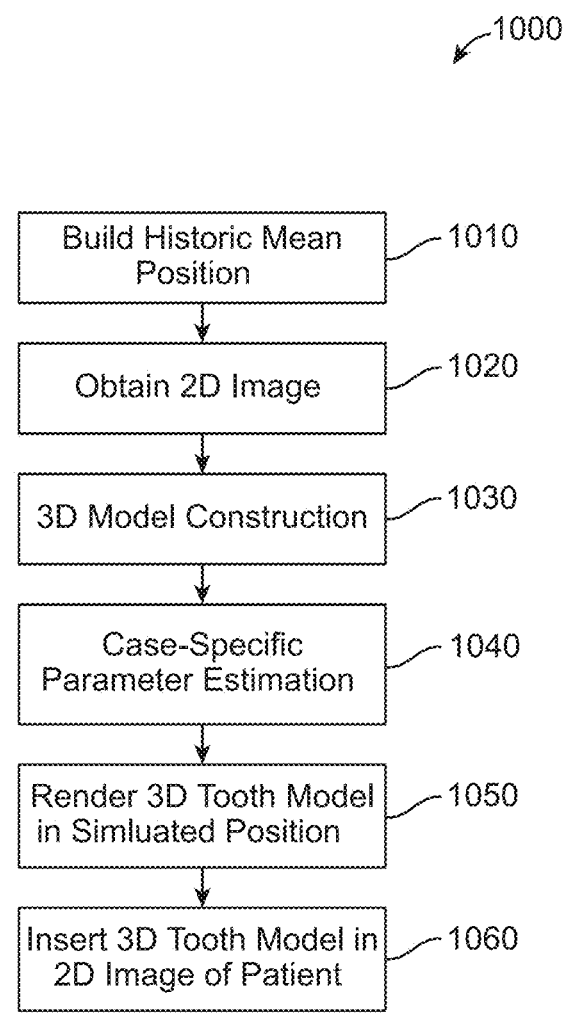
FIG. 10A depicts a method of simulating an estimated outcome of an orthodontic treatment on a patient's teeth, in accordance with one or more embodiments herein.

FIG. 10A depicts a method 1000 for simulating an estimated and/or intended outcome of a dental treatment plan on a patient's teeth, in accordance with one or more embodiments herein.

At block 1010, a model of a mean set of teeth arches is built. In some embodiments, the model is a parametric 3D model of a mean arch based on a set of historic scanned arches and/or arches representing idealized arch forms. In some embodiments, the scans are from the initial positions of patient's teeth. In some embodiments the scans are from patients after they have completed orthodontic treatment. In still other embodiments, the scans are taken without regard to whether the patient has undergone orthodontic treatment or not. In some implementations, the historic and/or idealized cases may represent arch models of treated patients (e.g., of patients who in the past have undergone treatment) and/or idealized arch models representing intended outcomes of various forms of orthodontic treatment. Block 1010 may include the process 350 as described with respect to FIG. 3B. At block 1010, cases are acquired. The cases may be retrieved from a datastore and may include previously scanned and segmented arch models.

The arches may also be aligned. Each arch in the datastore may aligned at a plurality of locations. For instance, each arch may be aligned at the following three locations: between the central incisors and at each distal end of the left and right side of each arch. For example, FIG. 4 shows a set of arches 400 aligned at location between the central incisors 410, at the left distal end of the arch 430, and the right distal end of the arch 420.

In some embodiments, determining a mean arch model and determining arch model distributions includes performing sub steps. For example, each historic arch may be rescaled to determine $\Phi$, then each arch is averaged to determine $T_\tau^C$, then the individual tooth local transformations are determined and compared to $T_\tau^C$ to determine $T_\tau$, then after aligning each tooth $\beta_\tau$ is determined.

The distribution estimation for case specific parameters are also determined. For example, each tooth's relative shape, location, and rotation are determined in order to build the distribution for each case specific parameter. For example the distribution of the $a_\tau^i$, the coefficients for the principal components, for the surface model of the each respective tooth in all of the retrieved models is determined.

The location and orientation of each tooth is averaged to determine a mean location for each tooth and the orientation of each tooth is averaged to determine a mean orientation for each tooth. The mean location and orientation are used to determine $T_\tau^C$.

Finally, the mean of the distribution of the estimation for case specific parameters may be used as the generic parameters of mean tooth position and mean tooth shape.

At block 1020, a 2D image of a patient is captured. In some embodiments, the 2D image includes the mouth of the patient and one or more images of the face, head, neck, shoulders, torso, or the entire patient. The 2D image of the patient may include an image of the patient with their mouth in one or more positions; for example, the patient's mouth may be a smiling position, such as a social smiling position, a repose position with relaxed muscles and lips slightly parted, or anterior retracted open bite or closed bite positions.

In some embodiments the image of the patient is obtained, e.g., taken with an image capture system. The image may be captured with a lens at a predetermined focal length and at a distance from the patient. In some implementations, the image of the patient is obtained from a computer-storage device, a network location, a social media account, etc. The image may be captured remotely and then received for processing. The image may be a series of images of video captured from one or more perspectives. For example, the images may include one or more of a frontal facial image and a profile image, including one or more three-quarter profile images and full profile images.

At block 1030, a 3D model of the patient's teeth is constructed from the 2D image of the patient's teeth. The 3D model may be based on a parametric model constructed according to the process described with respect to FIG. 6, wherein the edges of the oral features of the patient are determined. For example, the edges of one or more of the patient's teeth, lips, and gingiva may be determined. An initial determination of the patient's lips (for example, the inner edges of the lips that define the mount opening), teeth, and gingiva contours may be identified by a machine learning algorithm, such as a convoluted neural network.

Then, the initial contours may be extracted from the image. The pixels that denote the contours may then undergo binarization. The binarized tooth contours are thinned, whereby the contour's thickness is reduced to, for example, a single pixel in width, forming a thinned contour.

Using the contours, either thinned or otherwise, parameterized 3D teeth and arch models are matched to each of the patient's teeth that are depicted in the 2D image of the patient. The matching is based on the contours, determined above. After identifying and modeling the teeth and arch, or as part of such a process, missing or broken teeth may be inserted into the parameterized 3D tooth and arch model.

At block 1040, case specific parameters are estimated. In some embodiments, the case specific parameters may be determined at block 1030 as part of the model construction according to the process described, for example, at FIG. 6. During the matching process or at block 1040, the case specific parameters of a parametric arch model are varied and iterated through until a match between the parametric arch model and the teeth depicted in the 2D image is found. This match may be determined based on a projection of the edges of a silhouette of the parametric model match with the edges of the lips, teeth, and gingiva identified in the 2D image, as described herein.

Figure 11:
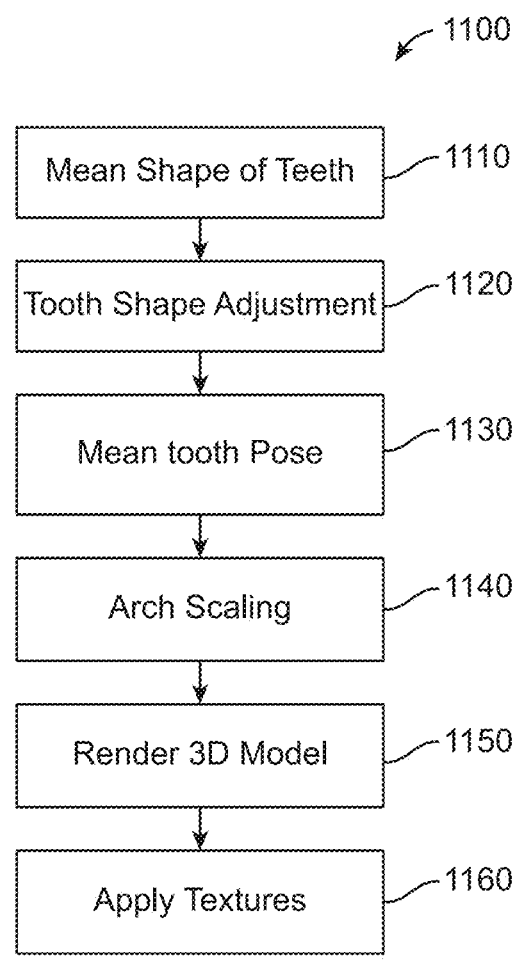
FIG. 11 shows an example of a method for rendering teeth according to an estimated outcome of a dental treatment plan, in accordance with one or more embodiments herein.

At block 1050 the patient's teeth are rendered according to a simulated outcome of a dental treatment plan using the patient's case specific parameters for tooth shape or arch scale, but using the mean value for tooth position. FIG. 11 shows an example of a method for rendering teeth according to an and/or intended outcome of a dental treatment plan using the appropriate case specific and mean parameter values.

Optionally, at block 1050, other changes, such as gingiva line adjustment, jaw position adjustment, missing tooth replacement, or broken tooth repair, can be applied to the 3D model before rendering into 2D form. In some embodiments, the edges and other features of the model, such as lips, gingiva line, and missing or broken teeth, may be altered to display simulated results of treatment procedures or to adjust the 2D patient image for customized viewing. For example, the user may adjust the gingiva line to simulate gum treatments. In another example, the user may opt to show, hide, or repair missing or chipped teeth to simulate tooth repair or replacement procedures. In this case an ideal tooth, based on the ideal parameters discussed above, may be used to replace the missing or damaged tooth. The missing or damaged tooth may be replaced based on one of the teeth in the historic datastore, or with a patient's own tooth, such as a corresponding tooth from the opposite side of the patient's arch may be used. For example, if the left upper canine is missing or chipped, a mirrored model of the patient's right upper canine may be used in the position of the missing left upper canine. In another example, the user may opt to adjust jaw position in the pre- or post-treatment simulated image to simulate appearances with the jaw open, closed, or partially open. A jaw position parameter can be defined by distance between a tooth surface in the upper jaw and a tooth surface in the lower jaw, such as the distance between the incisal surface of the upper central incisor in relation to the incisal surface of the lower central incisor. The jaw position parameter can be defined and varied by the user. The gingiva line can be adjusted by replacing the patient gingiva line mask shape with the mean gingiva line mask shape from the historic mean shape database. Display of gingiva line adjustment can be optionally selected or adjusted by the user. Missing or broken teeth can be replaced with a mean tooth shape from the historic mean shape database. Display of missing tooth replacement or broken tooth repair can be optionally selected by the user. Simulated treatments or viewing customizations may be rendered, for example, on a screen for viewing by the user, a patient, or a dental professional.

At block 1060 the 3D model is inserted into 2D image of the patient. For example, the 3D rendering of the teeth may be placed in the mouth of the patient as defined by the lip contours determined at block 1030 as part of the model construction process. In some embodiments, at block 1060 the textures model is adjusted to simulate clinical beautification treatments. For example, color may be adjusted to simulate tooth whitening procedures. A mask can be generated from at 2D projection of the 3D tooth model. The mask can be applied to the 2D image of the patient's teeth, in either the initial or final positions. Color adjustment or whitening can be further applied to the mask region. Color adjustment and whitening parameters can be optionally selected and adjusted by the user.

Simulated treatments or viewing customizations performed at block 1050 or block 1060 can be selected, de-selected, or adjusted by the user on the projected 2D image. Parameters can be adjusted to simulate treatments, such as whitening, gum line treatments, tooth replacement, or tooth repair, or for viewing customization, such as to display jaw open, closed, or partially open. In one example, the user can optionally adjust a color parameter to simulate tooth whitening. The user can adjust the color parameter to increase or decrease the degree of tooth whitening. In another example, the user can optionally adjust a gingiva line parameter to simulate gum line treatments or changes as a result of dental hygiene. The user can adjust the gingiva line parameter to raise the gingiva line (decrease the amount of exposed tooth surface) to simulate gum recovery, such as resulting from improved dental hygiene or gum line treatments, or lower the gingiva line (increase the amount of exposed tooth surface) to simulate gum recession, such as resulting from poor dental hygiene. In another example, the user can optionally select a tooth replacement parameter. The user can select the tooth replacement parameter to replace one or more missing, broken, or damaged teeth with an ideal tooth, such as with a tooth from the historic datastore or with a patient's own tooth. In another example, the user can optionally adjust a jaw line parameter for customized viewing of jaw position. The user can increase a distance between a tooth in the upper jaw in relation to a tooth in the lower jaw to simulate jaw opening or decrease the distance between the tooth in the upper jaw in relation to the tooth in the lower jaw to simulate jaw closing. In this case, the user can simulate the appearance of orthodontic, cosmetic, or clinical treatments in a variety of jaw positions.

Figure 10B:
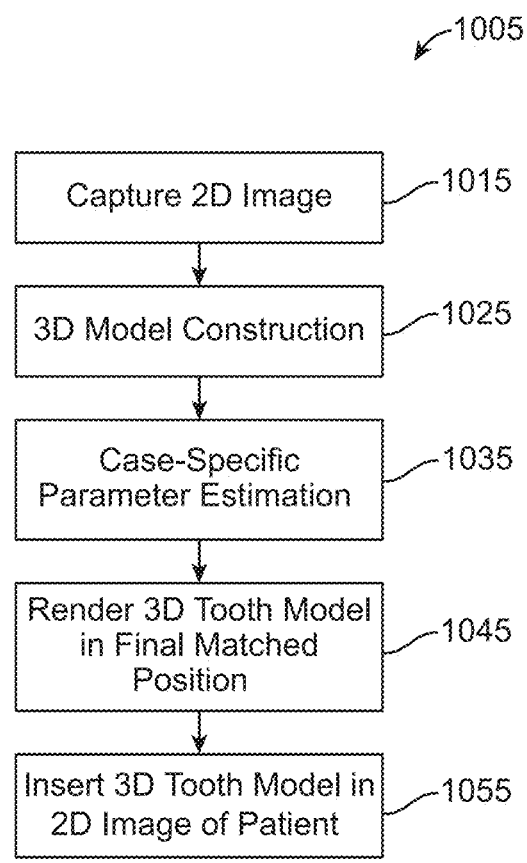
FIG. 10B depicts a method of simulating orthodontic treatment of a patient, based on matching tooth shape parameters, in accordance with one or more embodiments herein.

FIG. 10B depicts a process 1005 for simulating a final treatment position of a patient's teeth using a matched arch identified from a parameterized search of the treatment plan datastore.

At block 1015, a 2D image of a patient is captured, as described at block 1020 of FIG. 10A, and, at block 1025, the 3D model of the patient's teeth is constructed from the 2D image of the patient's teeth as at block 1030 of FIG. 10A. At block 1035 case specific parameters are estimated as at block 1040 of FIG. 10A.

At block 1045 the tooth shape parameters of the patient's teeth from the 3D model are used to perform a parameterized search of the treatment plan datastore. When matching the shapes of teeth of the patient with the shapes of teeth of historic treatment in the datastore, the shapes the teeth in the patient's parameterized 3D model are compared to the parameterized shapes of the teeth in each of the historic records in the treatment datastore. When a match between the teeth shapes is found, the final tooth positions and orientations, or the final arch model of the match record may be used in the simulated treatment plan. A parameterized template arch may be identified based on comparison of tooth shape parameters to identify a matched template arch. In some embodiments, the match may be based on, for example, the closest match template arch. In some embodiments, the template shape may be loaded into memory or retrieved from memory. The template shape may also be initialized as a set of matrices, one for each tooth. Once a match is found in a record within treatment datastore, the final arch model from the match record is retrieved and may be used as a basis for the patient's target final tooth positions.

In some embodiments, the tooth locations and orientations in the matched record are used as the basis for the tooth locations and orientations for the patient's target final tooth positions. When using the tooth locations and orientations, the patient's parameterized arch model may be modified with the tooth locations and orientations in the matched record or the match record may be updated with the shape of the patient's teeth. In some embodiments, the model of each of the patient's teeth with an unaltered tooth shape is placed in the final tooth pose determined from the matched record. In some embodiments, the model of each of the patient's teeth with an adjusted shape, such as the teeth shapes from the matched record, is placed in the final tooth pose determined from the matched record. Optionally, a tooth pose adjustment can be performed to adjust the positions of the teeth in the final tooth pose In some embodiments, the final arch model from the matched record is used as the simulated final position for the patient's treatment in the 2D rendering. In some embodiments, the teeth of the final arch model from the matched record are placed in positions according to the positions of the teeth in the patient's 2D photo. Alternately, the teeth of the final arch model are placed in positions according to the positions of the teeth in the patient's parameterized 3D model. The final arch model, optionally with positions adjusted according to the patient's 2D photo or 3D model, may be used as the simulated position in the 2D rendering.

The shape of the template teeth may be adjusted based on the patient's parameterized 3D model to more closely match the patient's tooth shapes. Optionally, a principal component analysis shape adjustment can be performed on the template teeth shape. After the shape adjustment is completed, in some embodiments, the adjusted shape may be rendered, for example, on a screen for viewing by a user, patient, or dental professional. In some embodiments, the adjusted shape may be stored into memory. The adjusted shape may also be stored as a set of matrices, one for each tooth. In some embodiments, the patient's teeth are substituted for the teeth in the matching template from the treatment datastore.

The template arch may be scaled such that it is generated with according to the patient's tooth and arch size. In some embodiments, the template arch scaling factor $\Phi$ is based on the particular tooth and arch of a particular patient, as discussed above. In some embodiments, the template arch scaling factor may also be based on one or more of the image size of the 2D image of the patient, for example, when scaling the 3D model for integration into a 2D image. In some embodiments, the size of each template tooth and the template arch is adjusted such that the scaled template arch matches the size of a patient's arch as determined, for example, by the size of the teeth and arch in the patient's scanned arch, or otherwise, as discussed herein. In some embodiments, the scaled template arch may be rendered, for example, on a screen for viewing by a user, patient, or dental professional. In some embodiments, the scaled template arch may be stored in memory. The scaled template arch may also be stored as a set of matrices, one for each tooth in the tooth pose. In some embodiments, the ideal template tooth shapes may be placed in their corresponding scaled position and size before the shapes of the teeth are adjusted.

At block 1045 simulated treatments or viewing customizations, such as gingiva line adjustment, jaw position, missing tooth insertion, or broken tooth repair, can be applied to the 3D model before rendering into 2D form. Simulated treatments or viewing customizations changes may be applied and adjusted as described at block 640.

At block 1055 the 3D model is inserted into 2D image of the patient. For example, the 3D rendering of the teeth may be placed in the mouth of the patient as defined by the lip contours determined at block 1025 as part of the model construction process. Rendering may be performed with or without the simulated treatments or viewing customizations implemented at block 1045. In some embodiments, at block 1055 the textures model is adjusted to simulate clinical treatments. For example, color may be adjusted to simulate tooth whitening procedures. A mask can be generated from at 2D projection of the 3D tooth model. The mask can be applied to the 2D image of the patient's teeth, in either the initial or final positions. Color adjustment or whitening can be further applied to the mask region. Color adjustment and whitening parameters can be optionally selected and adjusted by the user.

Simulated treatments and viewing customizations performed at block 1045 or block 1055 can be selected, de-selected, or adjusted by the user on the projected 2D image. Parameters can be adjusted to simulate treatment, such as whitening, gum line treatments, tooth replacement, or tooth repair, or for viewing customization, such as display jaw open, closed, or partially open.

FIG. 11 shows an example of a method for rendering teeth according to an estimated and/or intended outcome of a dental treatment plan based on a parametric model of the patient's arch using patient-derived values for the case-specific parameters of scale and tooth shape, but using a mean value (e.g., one derived from historical and/or idealized arches) for tooth position.

At block 1110 the mean shape, $S_\tau^C$, of each tooth is determined. In some embodiments, the mean shape may be based on the mean shape of a set of scanned arches, as discussed herein. In some embodiments, the mean shape may be rendered, for example, on a screen for viewing by a patient or dental professional. In some embodiments, the mean shape may be loaded into memory or retrieved from memory. The mean shape may also be initialized as a set of matrices, one for each tooth.

At block 1120, a principal component analysis shape adjustment is performed on the mean shape of the teeth, S. For each tooth in the model, the case specific coefficients for the principal components, $a_\tau^i$, are applied to the principal component, $B_\tau^i$. After the shape adjustment is completed, in some embodiments, the adjusted shape may be rendered, for example, on a screen for viewing by a patient or dental professional. In some embodiments, the adjusted shape may be stored into memory. The adjusted shape may also be stored as a set of matrices and/or data structures, e.g., one for each tooth.

At block 1130, the mean tooth pose is determined. In some embodiments, the mean tooth pose may be based on the mean tooth pose of a set of scanned arches, as discussed above. In some embodiments, at block 1130, each adjusted tooth is placed in its corresponding mean location and orientation, as determined by the mean arch. In some embodiments, the mean tooth pose may be rendered, for example, on a screen for viewing by a patient or dental professional. In some embodiments, the mean tooth pose may be loaded into memory or retrieved from memory. The mean tooth pose may also be initialized as a set of matrices, one for each tooth in the tooth pose. In some embodiments, the mean tooth shapes from block 1110 may be placed in their corresponding mean tooth pose at block 1130 before the shapes of the teeth are adjusted at block 1120. In other words, the order of block 1120 and block 1130 may be swapped.

At block 1140, the arch is scaled such that it is generated with tooth dimensions according to the patient's tooth and arch size. In some embodiments, an arch scaling factor Φ is based on the particular tooth and arch of a particular patient, as discussed above. In some embodiments, at block 1140 the arch is adjusted such that the scaled arch matches the size of a patient's arch, as determined, for example, by size of the teeth and arch in the patient's scanned arch, or otherwise, as discussed herein. In some embodiments, the scaled arch may be rendered, for example, on a screen for viewing by a patient or dental professional. In some embodiments, the scaled arch may be stored in memory. The scaled arch may also be stored as a set of matrices, one for each tooth in the tooth pose. In some embodiments, the mean tooth shapes from block 1110 may be placed in their corresponding scaled position and size at block 1140 before the shapes of the teeth are adjusted at block 1120. In other words, the order of block 1120 and blocks 1130, and 1140 may be swapped such that block 1120 takes place after blocks 1130 and 1140.

Prior to rendering at block 1150 simulated treatment or viewing customizations, such as gingiva line adjustment, jaw position, missing tooth insertion, or broken tooth repair, can be applied to the 3D model. Simulated treatment or viewing customizations may be applied and adjusted as described at block 640. Simulated treatment or viewing customizations can be applied before or after arch scaling (e.g., before or after block 1140).

At block 1150, the 3D model of the patient's teeth determined at block 1140 is rendered for viewing or the final 3D model is stored for later on-screen rendering. The 3D model can be rendered for viewing or stored for later on-screen rendering with or without the simulated treatment or viewing customizations.

At block 1160, textures are applied to the 3D model of the patient's teeth in an estimated and/or intended final position. For example, textures determined based on a 2D image of the patient's teeth, for example, according to process 900 in FIG. 9, may be applied to the 3D model. In some embodiments, the texture application process of block 1160 may occur during or as part of the rendering process of block 1150. During texture application, either at block 1160 or during the rendering process of block 1150, textures model can be adjusted to simulate treatment or for customizable viewing. Simulated treatment or viewing customizations, including color adjustments, e.g., to simulate tooth whitening, can be applied either to the 3D model or may occur as part of the rendering process. Alternatively, color adjustment can be performed at described at block 1060. Simulated treatment and viewing customizations, color adjustment can be adjusted by the user.

Optionally, step 1110 can be replaced by a parameterized search of the treatment plan datastore to identify a matched template model based on the patient's tooth shape. Steps 1120 through 1160 can subsequently be implemented as described using the template arch and tooth shape in place of the mean arch or tooth shape to determine ideal tooth pose instead of mean tooth pose.

Figure 12:
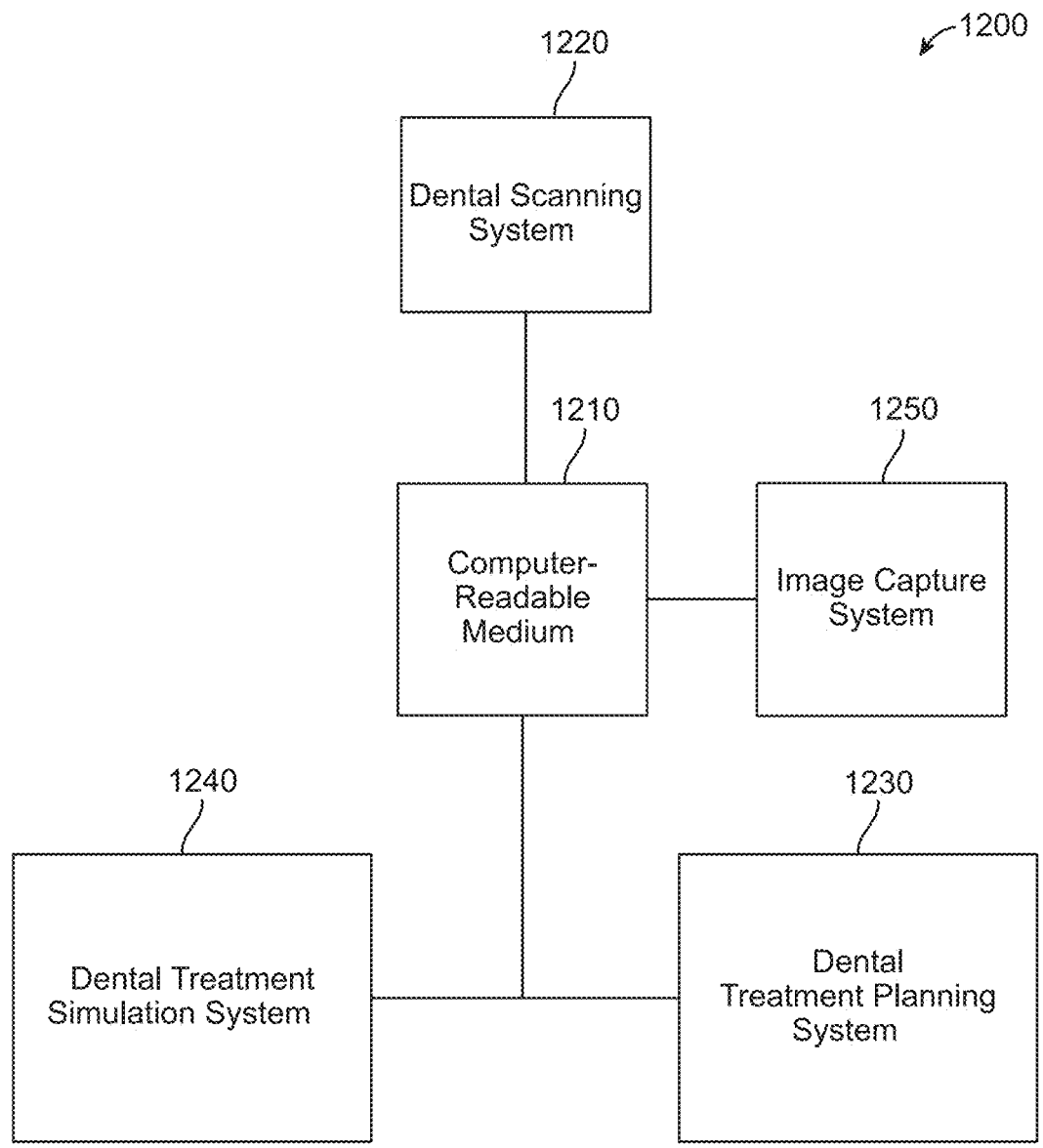
FIG. 12 depicts a system for simulating an estimated outcome of an orthodontic treatment, in accordance with one or more embodiments herein.

FIG. 12 depicts a system 1200 for simulating an estimated and/or intended outcome of an orthodontic treatment, in accordance with some embodiments. In the example of FIG. 12, the system 1200 includes a computer-readable medium 1210, a dental scanning system 1220, dental treatment planning system 1230, a dental treatment simulation system 1240 and an image capture system 1250. One or more of the elements of the system 1200 may include elements of such as those described with reference to the computer system shown in FIG. 20. One or more elements of the system 1200 may also include one or more computer readable media including instructions that when executed by a processor, for example, a processor of any of the systems 1220, 1230, 1240, and 1250 cause the respective system or systems to perform the processes described herein.

The dental scanning system 1220 may include a computer system configured to capture one or more scans of a patient's dentition. The dental scanning system 1220 may include a scan engine for capturing 2D images of a patient. Such images may include images of the patient's teeth, face, and jaw. The images may also include x-rays or other subsurface images of the patient. The scan engine may also capture 3D data representing the patient's teeth, face, gingiva, or other aspects of the patient.

The dental scanning system 1220 may also include a 2D imaging system, such as a still or video camera, an x-ray machine, or other 2D imager. In some embodiments, the dental scanning system 1220 also includes a 3D imager, such as an intraoral scanner or an impression scanner. The dental scanning system 1220 and associated engines and imagers can be used to capture the historic scan data for use in determining the historic mean parameters of a 3D parametric dental model, as described with reference to FIGS. 1-11 herein. The dental scanning system 1220 and associated engines and imagers can be used to capture the 2D images of a patient's face and dentition for use in building a 3D parametric model of the patient's teeth, as described for example, with reference to FIGS. 1-11 herein.

The dental treatment simulation system 1240 may include a computer system configured to simulate one or more estimated and/or intended outcomes of a dental treatment plan. In some implementations, the dental treatment simulation system 1240 obtains photos and/or other 2D images of a consumer/patient. The dental treatment simulation system 1240 may further be configured to determine tooth, lip, gingiva, and/or other edges related to teeth in the 2D image. As noted herein, the dental treatment simulation system 1240 may be configured to match tooth and/or arch parameters to tooth, lip, gingiva, and/or other edges. The dental treatment simulation system 1240 may also render a 3D tooth model of the patient's teeth. The dental treatment simulation system 1240 may gather information related to historical and/or idealized arches representing an estimated outcome of treatment. The dental treatment simulation system 1240 may, in various implementations, insert, align, etc. the 3D tooth model with the 2d image of the patient in order to render a 2D simulation of an estimated outcome of orthodontic treatment. The dental treatment simulation system 1240 may include a photo parameterization engine which may further include an edge analysis engine, an EM analysis engine, a course tooth alignment engine, and a 3D parameterization conversion engine. The dental treatment simulation system 1240 may also include a parametric treatment prediction engine which may further include a treatment parameterization engine, a scanned tooth normalization engine, and a treatment plan remodeling engine. The dental treatment simulation system 1240 and its associated engines may carry out the processes described above with respect to FIGS. 5-9.

The dental treatment planning system 1230 may include a computer system configured to implement treatment plans. The dental treatment planning system 1230 may include a rendering engine and interface for visualizing or otherwise displaying the simulated outcome of the dental treatment plan. For example, the rendering engine may rendering the visualizations of the 3D models described herein, for example, at block 140 of FIG. 1, at blocks 640, 650, 660 of FIG. 6, process 800, described with reference to FIG. 8, at blocks 910, 920, 930 of FIG. 9, block 1150 of FIG. 10, and block 1150 of FIG. 11. The dental treatment planning system 1230 may also determine an orthodontic treatment plan for moving a patient's teeth from an initial position, for example, based in part on the 2D image of the patient's teeth, to a final position. The dental treatment planning system 1230 may be operative to provide for image viewing and manipulation such that rendered images may be scrollable, pivotable, zoomable, and interactive. The dental treatment planning system 1230 may include graphics rendering hardware, one or more displays, and one or more input devices. Some or all of the dental treatment planning system 1230 may be implemented on a personal computing device such as a desktop computing device or a handheld device, such as a mobile phone. In some embodiments, at least a portion of the dental treatment planning system 1230 may be implemented on a scanning system, such as the dental scanning system 1220. The image capture system 1250 may include a device configured to obtain an image, including an image of a patient. The image capture system may comprise any type of mobile device (iOS devices, iPhones, iPads, iPods, etc., Android devices, portable devices, tablets), PCs, cameras (DSLR cameras, film cameras, video cameras, still cameras, etc.). In some implementations, the image capture system 1250 comprises a set of stored images, such as images stored on a storage device, a network location, a social media website, etc.

Figure 13:
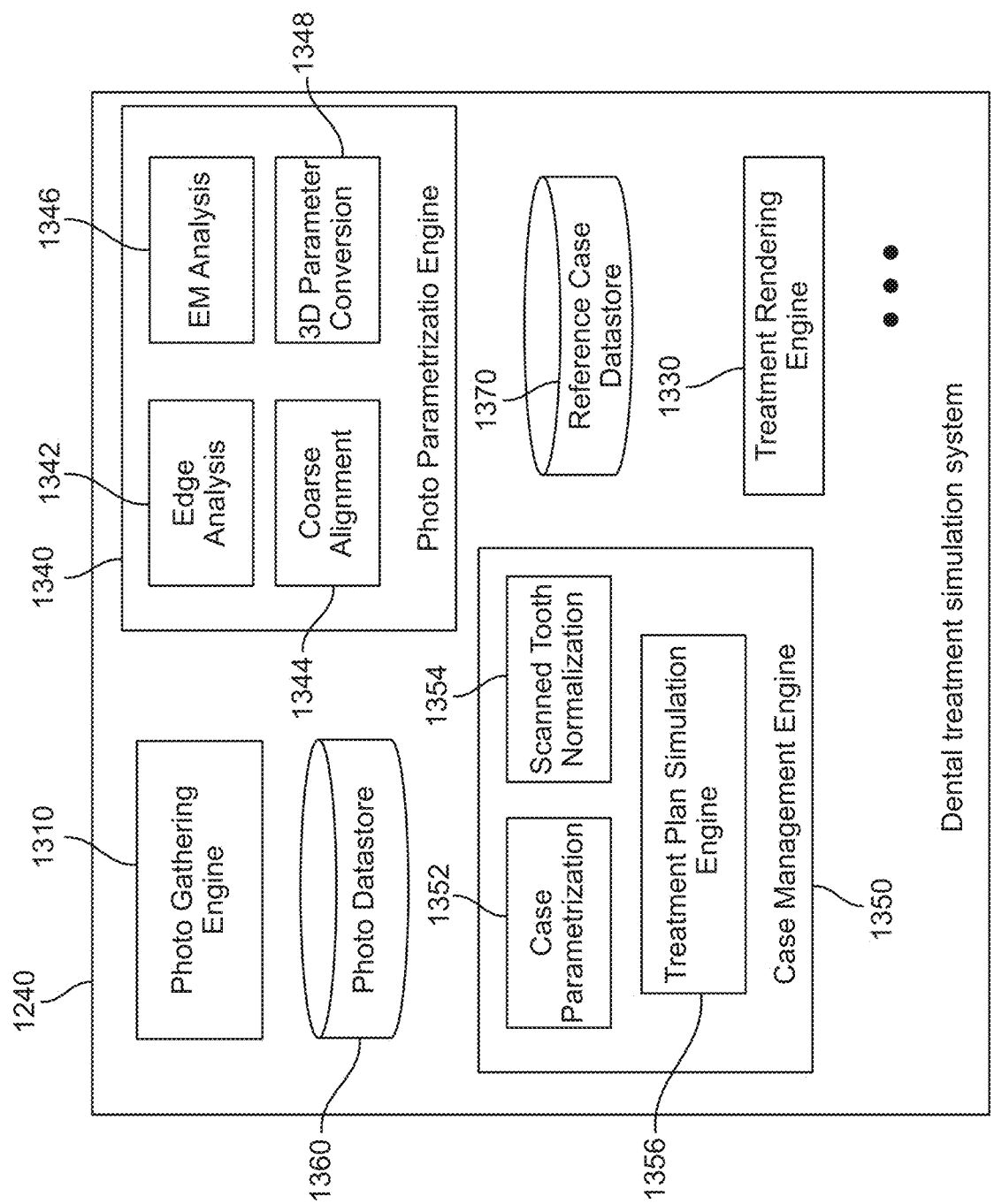
FIG. 13 depicts an example of one or more of the elements of the estimated orthodontic treatment simulation system, in accordance with one or more embodiments herein.

FIG. 13 shows an example of one or more of the elements of the dental treatment simulation system 1240, in accordance with some embodiments. In the example of FIG. 13, the dental treatment simulation system 1240 includes a photo gathering engine 1310, a photo datastore 1360, a photo parameterization engine 1340, a case management engine 1350, a reference case datastore 1370, and a treatment rendering engine 1330.

The photo gathering engine 1310 may implement one or more automated agents configured to retrieve a selected photo of a patient from the photo datastore 1360, the image capture system 1250, and/or a scan from the dental scanning system 1220. The photo gathering engine may then provide the photo or photos to the photo parameterization engine 1340. The photo gathering engine may then provide the photo or photos to the photo parameterization engine 1340 and/or other modules of the system.

The photo datastore 1360 may include a datastore configured to store photos of patients, such as their facial photos. In some embodiments, the photos are 2D images that include the mouth of the patient and one or more images of the face, head, neck, shoulders, torso, or the entire patient. The 2D image of the patient may include an image of the patient with their mouth in one or more positions; for example, the patient's mouth may be a smiling position, such as a social smiling position, a repose position with relaxed muscles and lips slightly parted, or anterior retracted open bite or closed bite positions. In some embodiments the image of the patient is taken with an image capture system. The image may be captured with a lens at a predetermined focal length and at a distance from the patient. The image may be captured remotely and then received for processing. The image may be a series of images of video captured from one or more perspectives. For example, the images may include one or more of a frontal facial image and a profile image, including one or more three-quarter profile images and full profile images.

The photo parameterization engine 1340 may implement one or more automated agents configured to build a parametric 3D model based on the 2D image of the patient from the photo datastore 1360 and the parametric model and mean data from the parametric treatment prediction engine. The edge analysis engine 1342 may implement one or more automated agents configured to determine the edges of the teeth, lips and gingiva within the photo of the patient. For example as described with respect to FIG. 6. In particular, an initial determination of the patient's lips (for example, the inner edges of the lips that define the mount opening), teeth, and gingiva contours may be identified by a machine learning algorithm, such as a convoluted neural network.

Then, the initial contours may be extracted from the image. The pixels that denote the contours may then undergo binarization. The binarized tooth contours are thinned, whereby the contour's thickness is reduced to, for example, a single pixel in width, forming a thinned contour.

Using the contours, either thinned or otherwise, parameterized 3D teeth and arch models are matched to each of the patient's teeth that are depicted in the 2D image of the patient. The matching is based on the contours, determined above.

The coarse alignment engine 1344 may implement one or more automated agents configured to receive the 2D image and/or the associated edges and performs a coarse alignment between the identified edges and the mean tooth models, for example, as described with reference to FIG. 7A, wherein the respective centers of the teeth in the 2D image and the silhouette of the parametric tooth may be aligned before the 2D image and/or associated edges, along with the silhouettes and their associated tooth parameters are sent to the EM engine 1346.

The expectation maximization (EM) engine 1346 may implement one or more automated agents configured to perform an expectation-maximization analysis between the edges of the 2D image and the parameters of the 3D parametric model, for example as described with respect to FIG. 7A, and in particular, blocks 720, 730, and 740.

Once the EM analysis engine 1346 completes the matching of the parametric 3D model to the 2D image of the patient, the parametric results are sent to the 3D parameter conversion engine 1348, which may convert the output principle component analysis of the EM analysis engine to case-specific parameters that define a 3D model of the patient's teeth according to a parametric model for use by the parametric treatment prediction engine 1350, as described above.

The case management engine 1350 may include a case parameterization engine 1352, a scanned tooth normalization engine 1354, and a treatment plan simulation engine 1356. The case management engine 1350 may implement one or more automated agents configured to define the parametric model used to represent the teeth and arch of patients, determine the mean data to parametrically represent the mean positions of a patient's teeth and arch based on the treatment plans retrieved from the treatment plan datastore 1370, and simulate the treatment of a particular patient's teeth based on the parametric model, the mean tooth positions, and a patient's particular teeth.

The case parameterization engine 1352 may implement one or more automated agents configured to define the parametric 3D model for use in modeling teeth. For example, the parametric 3D model may be defined as described above with reference to eq. (2). More than just defining the equation, treatment parameterization engine 1352 may also define the schema for the parameters. For example, the $T_\tau$, which represents tooth positions, may be defined as a 4*4 matrix including tooth position and rotation in 3 axis. Similarly, $a_\tau^i$, which represents tooth shape, may be defined as an 2500*3 matrix, where each vertex of the sphere is mapped to a location on the surface of the tooth model, each location of a vertex being x, y, and z special locations. For lower or higher definition models, fewer or greater vertices may be used. Further discussion of the parameters defined by the treatment parameterization engine 1352 are descried elsewhere herein, for example with respect to FIGS. 2-5.

The scanned tooth normalization engine 1354 may implement one or more automated agents configured to parameterize the scanned teeth of a set of treatment plans gathered from the treatment plan datastore 1370 and then determines the mean set of general generic parameters for the parametric model. The scanned tooth normalization engine 1354 may carry out process 350, as described with reference to FIG. 3B. For example, the scanned tooth normalization engine 1354 may align the arches within the historic cases retrieved from the datastore 1370. Each arch in the datastore is aligned at three locations: between the central incisors and at each distal end of the left and right side of each arch. Each tooth's position and orientation is then determined based on its location and orientation with reference to the alignment points.

The scanned tooth normalization engine 1354 may implement one or more automated agents configured to determine the distributions of the parameters among the cases. For example, each historic arch may be rescaled to determine Φ, then each arch is averaged to determine $T_\tau^C$, then the individual tooth local transformations are determined and compared to $T_\tau^C$ to determine $T_\tau$, then after aligning each tooth $\beta_\tau$ is determined.

From this data, each tooth's relative shape, location, and rotation are determined in order to build the distribution for each case specific parameter. For example the distribution of the $a_\tau^i$, the coefficients for the principal components, for the surface model of the each respective tooth in all of the retrieved models is determined.

The location and orientation of each tooth is averaged to determine a mean location for each tooth and the orientation of each tooth is averaged to determine a mean orientation for each tooth. The mean location and orientation are used to determine $T_\tau^C$.

In some embodiments, the scanned teeth of a set of treatment plans gathered from the treatment plan datastore can be used to generate a template datastore of parameterized template models. The scanned tooth normalization engine 1354 may align the arches within the historic cases retrieved from the reference case datastore 1370. Each arch in the reference case datastore is aligned at three locations: between the central incisors and at each distal end of the left and right side of each arch. Each tooth's position and orientation is then determined based on its location and orientation with reference to the alignment points. The parameters of the parameterized template models in the datastore are searchable. The datastore can be used to match patient 3D models (e.g., generated from 2D models or from 3D scans) to the closest template in the datastore based on tooth shape and arch shape to identify a matched template model. The closest matched template model can be used to determine the final tooth positions and orientations for the patient's teeth.

The treatment plan simulation engine 1356 may implement one or more automated agents configured to use the parametric model defined by the treatment parametrization engine 1352, the generic parameters from the scanned tooth normalization engine and the case specific parameters from the photo parameterization engine 1340 to simulate an estimated and/or intended outcome of a dental treatment plan of a specific patient's teeth, for example, as described with respect to FIGS. 10 and 11.

The treatment plan simulation engine 1356 retrieves or otherwise determines the mean shape, $S_\tau^C$. In some embodiments, the mean shape may be retrieved from scanned tooth normalization engine 1354. In some embodiments, the mean shape may be loaded into memory or retrieved from memory. The mean shape may also be initialized as a set of matrices, one for each tooth.

The treatment plan simulation engine 1356 performed a principal component analysis shape adjustment on the mean shape of the teeth, S. For each tooth in the model, the case specific coefficients as determined from the photo parametrization engine 1340 for the principal component, $a_\tau^i$, are applied to the principal component, $B_\tau^i$. After the shape adjustment is completed, in some embodiments, the adjusted shape may be rendered, for example, on a screen for viewing by a patient or dental professional. In some embodiments, the adjusted shape may be stored into memory. The adjusted shape may also be stored as a set of matrices, one for each tooth.

The treatment plan simulation engine 1356 determines the mean tooth pose. In some embodiments, the mean tooth pose may be based on the mean tooth pose of a set of scanned arches, as discussed above. In some embodiments, each adjusted tooth is placed in its corresponding mean location and orientation, as determined by the mean arch. In some embodiments, the mean tooth pose may be rendered, for example, on a screen for viewing by a patient or dental professional. In some embodiments, the mean tooth pose may be loaded into memory or retrieved from memory. The mean tooth pose may also be initialized as a set of matrices, one for each tooth in the tooth pose.

In some embodiments, the treatment plan remodeling engine 1356 uses the tooth position and orientation coordinates from the ideal parameterized datastore match and applies the shape and textures of the patient's 3D model generated from the 2D image to the tooth positions and orientations to generate an arch.

The treatment plan simulation engine 1356 scales the arch such that it is generated according to the patient's tooth and arch size. In some embodiments, the arch scaling factor Φ is based on the particular tooth and arch of a particular patient, as discussed above. In some embodiments, the arch is adjusted such that the scaled arch matches the size of a patient's arch, as determined, for example, by size of the teeth and arch in the patient's scanned arch, or otherwise, as discussed herein. In some embodiments, the scaled arch may be rendered, for example, on a screen for viewing by a patient or dental professional. In some embodiments, the scaled arch may be stored in memory. The scaled arch may also be stored as a set of matrices, one for each tooth in the tooth pose. The scaled arch may be sent to the treatment rendering engine 1330.

The treatment rendering engine 1330 renders the teeth and 2D image of the patient in a final position, as determined, for example, by the parametric treatment prediction engine 1350 and, in particular, the treatment plan simulation engine 1356 therein. The treatment rendering engine 1330 may carry out some of the processes described with reference to FIGS. 9, 10, and 11. In particular, the rendering processes descried with reference to FIGS. 9, 10, 11, and elsewhere herein.

Figure 14:
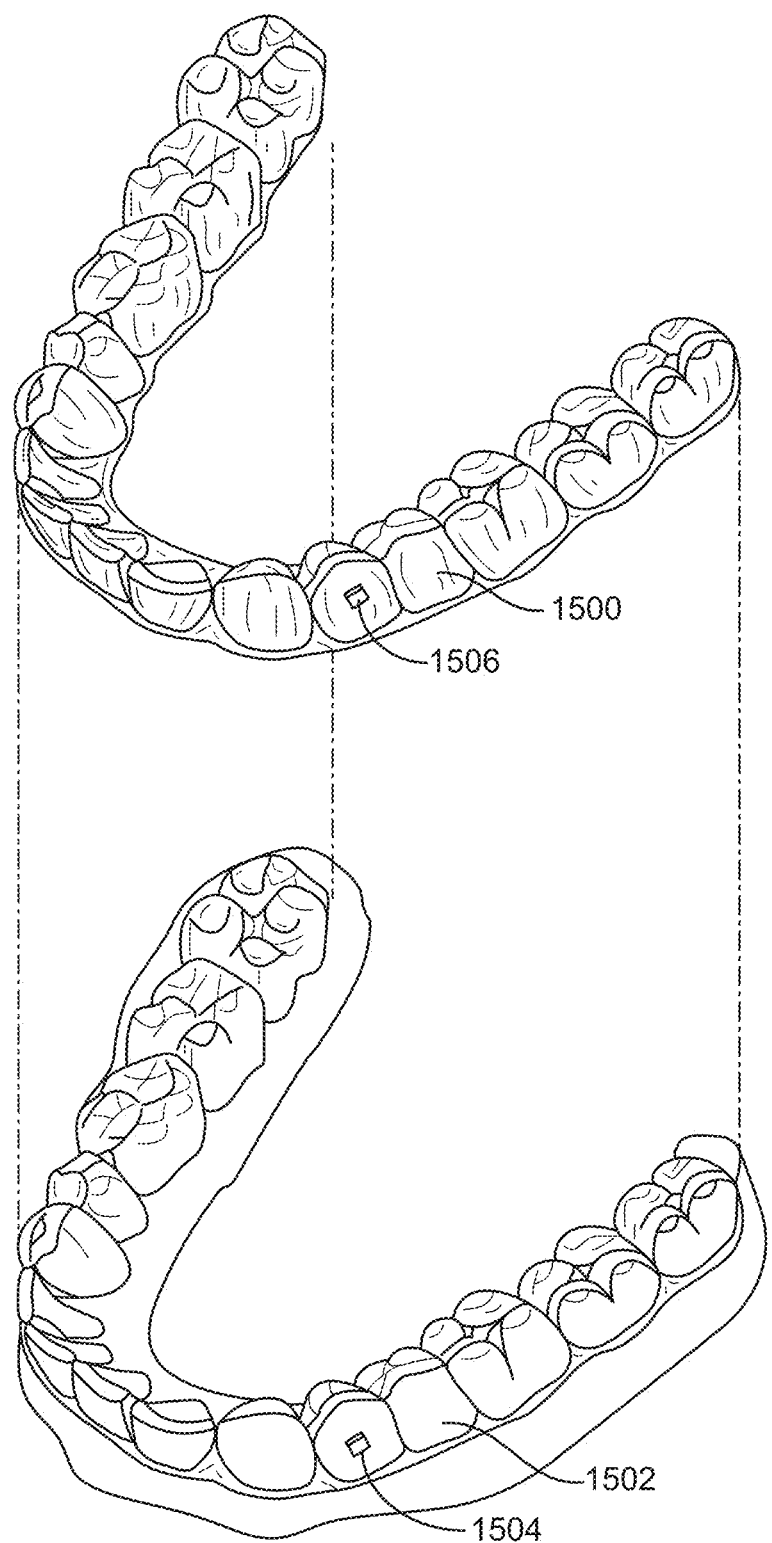
FIG. 14 illustrates a tooth repositioning appliance, in accordance with one or more embodiments herein.

FIG. 14 illustrates an exemplary tooth repositioning appliance or aligner 1500 that can be worn by a patient in order to achieve an incremental repositioning of individual teeth 1502 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient. In some embodiments, no wires or other means will be provided for holding an appliance in place over the teeth. In some cases, however, it may be desirable or necessary to provide individual attachments or other anchoring elements 1504 on teeth 1502 with corresponding receptacles or apertures 1506 in the appliance 1500 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

Figure 15:
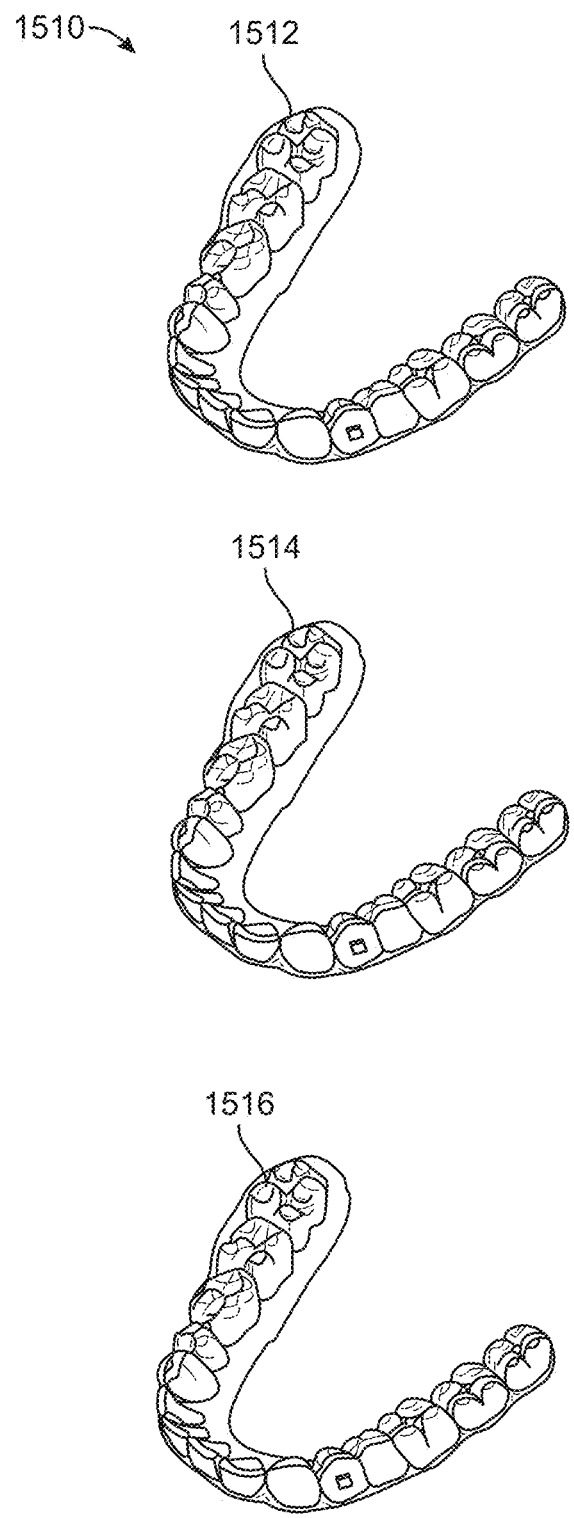
FIG. 15 illustrates a tooth repositioning system, in accordance with one or more embodiments herein.

FIG. 15 illustrates a tooth repositioning system 1510 including a plurality of appliances 1512, 1514, 1516. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement towards a target tooth arrangement by placing a series of incremental position adjustment appliances over the patient's teeth. For example, the tooth repositioning system 1510 can include a first appliance 1512 corresponding to an initial tooth arrangement, one or more intermediate appliances 1514 corresponding to one or more intermediate arrangements, and a final appliance 1516 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 16:
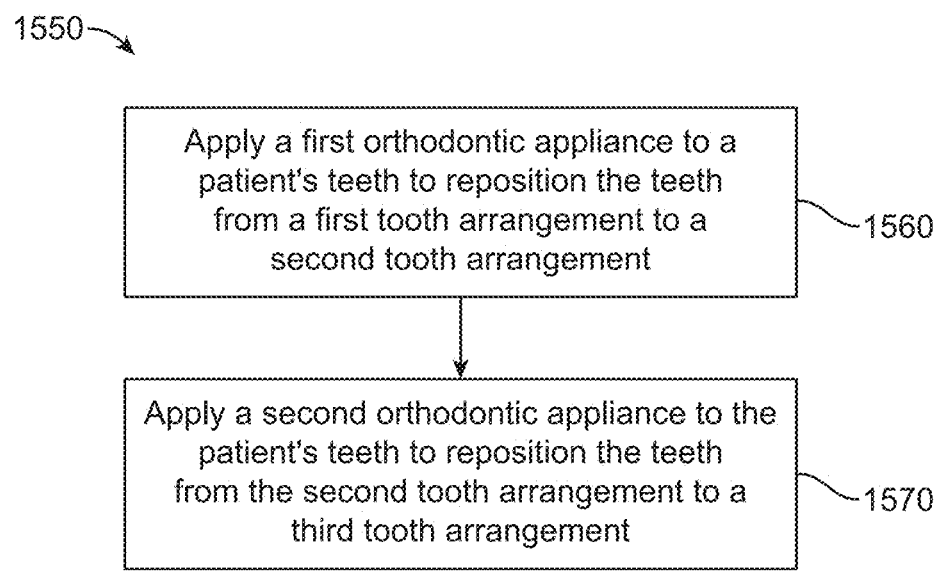
FIG. 16 illustrates a method of orthodontic treatment using a plurality of appliances, in accordance with one or more embodiments herein.

FIG. 16 illustrates a method 1550 of orthodontic treatment using a plurality of appliances, in accordance with embodiments. The method 1550 can be practiced using any of the appliances or appliance sets described herein. In block 1560, a first orthodontic appliance is applied to a patient's teeth in order to reposition the teeth from a first tooth arrangement to a second tooth arrangement. In block 1570, a second orthodontic appliance is applied to the patient's teeth in order to reposition the teeth from the second tooth arrangement to a third tooth arrangement. The method 1550 can be repeated as necessary using any suitable number and combination of sequential appliances in order to incrementally reposition the patient's teeth from an initial arrangement to a target arrangement. The appliances can be generated all at the same stage or in sets or batches (at the beginning of a stage of the treatment, at an intermediate stage of treatment, etc.), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry.

In some embodiments, the orthodontic appliances herein can be fabricated using a combination of direct and indirect fabrication techniques, such that different portions of an appliance can be fabricated using different fabrication techniques and assembled in order to form the final appliance. For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). The computer-based methods presented herein can improve the accuracy, flexibility, and convenience of appliance fabrication.

In some embodiments, computer-based 3D planning/design tools, such as Treat™ software from Align Technology, Inc., may be used to design and fabricate the orthodontic appliances described herein.

Figure 17:
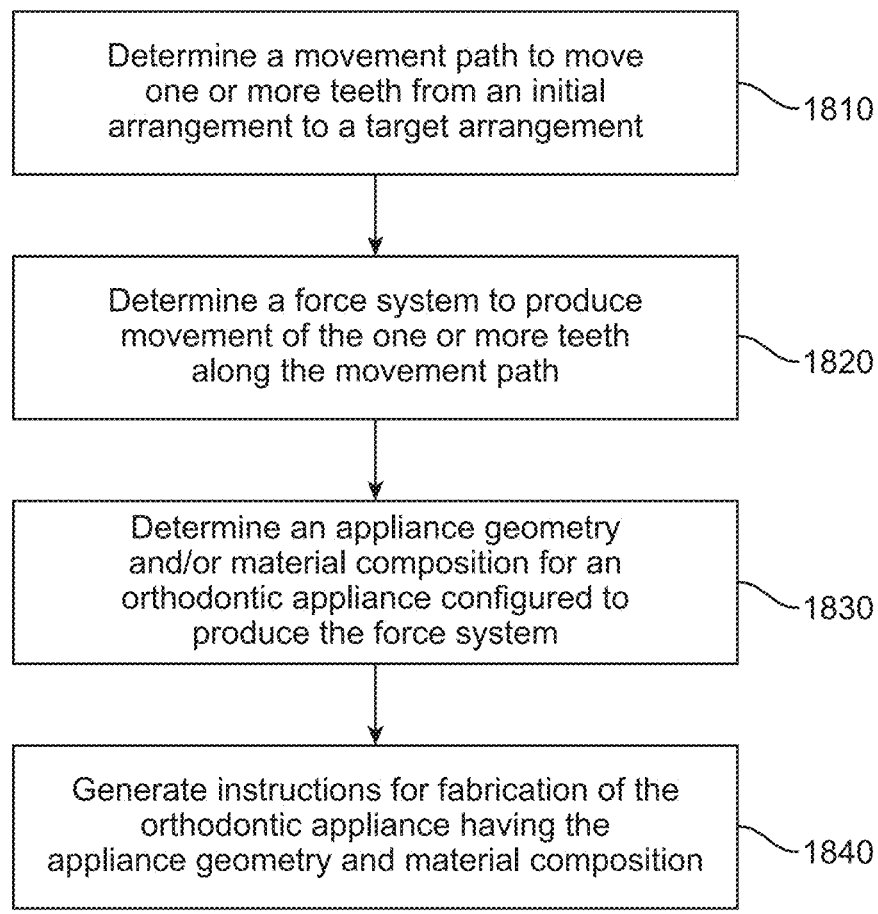
FIG. 17 illustrates a method for designing an orthodontic appliance, in accordance with one or more embodiments herein.

FIG. 17 illustrates a method 1800 for designing an orthodontic appliance to be fabricated, in accordance with embodiments. The method 1800 can be applied to any embodiment of the orthodontic appliances described herein. Some or all of the operations of the method 200 can be performed by any suitable data processing system or device, e.g., one or more processors configured with suitable instructions.

In block 1810, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 1820, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Determination of the force system can be performed in a variety of ways. For example, in some embodiments, the force system is determined on a patient-by-patient basis, e.g., using patient-specific data. Alternatively or in combination, the force system can be determined based on a generalized model of tooth movement (e.g., based on experimentation, modeling, clinical data, etc.), such that patient-specific data is not necessarily used. In some embodiments, determination of a force system involves calculating specific force values to be applied to one or more teeth to produce a particular movement. Alternatively, determination of a force system can be performed at a high level without calculating specific force values for the teeth. For instance, block 1820 can involve determining a particular type of force to be applied (e.g., extrusive force, intrusive force, translational force, rotational force, tipping force, torqueing force, etc.) without calculating the specific magnitude and/or direction of the force.

In block 1830, an appliance geometry and/or material composition for an orthodontic appliance configured to produce the force system is determined. The appliance can be any embodiment of the appliances discussed herein, such as an appliance having variable localized properties, integrally formed components, and/or power arms.

For example, in some embodiments, the appliance comprises a heterogeneous thickness, a heterogeneous stiffness, or a heterogeneous material composition. In some embodiments, the appliance comprises two or more of a heterogeneous thickness, a heterogeneous stiffness, or a heterogeneous material composition. In some embodiments, the appliance comprises a heterogeneous thickness, a heterogeneous stiffness, and a heterogeneous material composition. The heterogeneous thickness, stiffness, and/or material composition can be configured to produce the force system for moving the teeth, e.g., by preferentially applying forces at certain locations on the teeth. For example, an appliance with heterogeneous thickness can include thicker portions that apply more force on the teeth than thinner portions. As another example, an appliance with heterogeneous stiffness can include stiffer portions that apply more force on the teeth than more elastic portions. Variations in stiffness can be achieved by varying the appliance thickness, material composition, and/or degree of photopolymerization, as described herein.

In some embodiments, determining the appliance geometry and/or material composition comprises determining the geometry and/or material composition of one or more integrally formed components to be directly fabricated with an appliance shell. The integrally formed component can be any of the embodiments described herein. The geometry and/or material composition of the integrally formed component(s) can be selected to facilitate application of the force system onto the patient's teeth. The material composition of the integrally formed component can be the same as or different from the material composition of the shell.

In some embodiments, determining the appliance geometry comprises determining the geometry for a variable gable bend.

The block 1830 can involve analyzing the desired force system in order to determine an appliance geometry and material composition that would produce the force system. In some embodiments, the analysis involves determining appliance properties (e.g., stiffness) at one or more locations that would produce a desired force at the one or more locations. The analysis can then involve determining an appliance geometry and material composition at the one or more locations to achieve the specified properties. Determination of the appliance geometry and material composition can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMULIA (Abaqus) software products from Dassault Systèmes of Waltham, Mass.

Optionally, one or more appliance geometries and material compositions can be selected for testing or force modeling. As noted above, a desired tooth movement, as well as a force system required or desired for eliciting the desired tooth movement, can be identified. Using the simulation environment, a candidate appliance geometry and composition can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

Optionally, block 1830 can further involve determining the geometry of one or more auxiliary components to be used in combination with the orthodontic appliance in order to exert the force system on the one or more teeth. Such auxiliaries can include one or more of tooth-mounted attachments, elastics, wires, springs, bite blocks, arch expanders, wire-and-bracket appliances, shell appliances, headgear, or any other orthodontic device or system that can be used in conjunction with the orthodontic appliances herein. The use of such auxiliary components may be advantageous in situations where it is difficult for the appliance alone to produce the force system. Additionally, auxiliary components can be added to the orthodontic appliance in order to provide other desired functionalities besides producing the force system, such as mandibular advancement splints to treat sleep apnea, pontics to improve aesthetic appearance, and so on. In some embodiments, the auxiliary components are fabricated and provided separately from the orthodontic appliance. Alternatively, the geometry of the orthodontic appliance can be modified to include one or more auxiliary components as integrally formed components.

In block 1840, instructions for fabrication of the orthodontic appliance having the appliance geometry and material composition are generated. The instructions can be configured to control a fabrication system or device in order to produce the orthodontic appliance with the specified appliance geometry and material composition. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.). Optionally, the instructions can be configured to cause a fabrication machine to directly fabricate the orthodontic appliance with teeth receiving cavities having variable gable bends, as discussed above and herein. In alternative embodiments, the instructions can be configured for indirect fabrication of the appliance, e.g., by thermoforming.

Although the above blocks show a method 1800 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 200 may be performed with any suitable fabrication system or device, such as the embodiments described herein. Some of the blocks may be optional, and the order of the blocks can be varied as desired. For instance, in some embodiments, block 1820 is optional, such that block 1830 involves determining the appliance geometry and/or material composition based directly on the tooth movement path rather than based on the force system.

Figure 18:
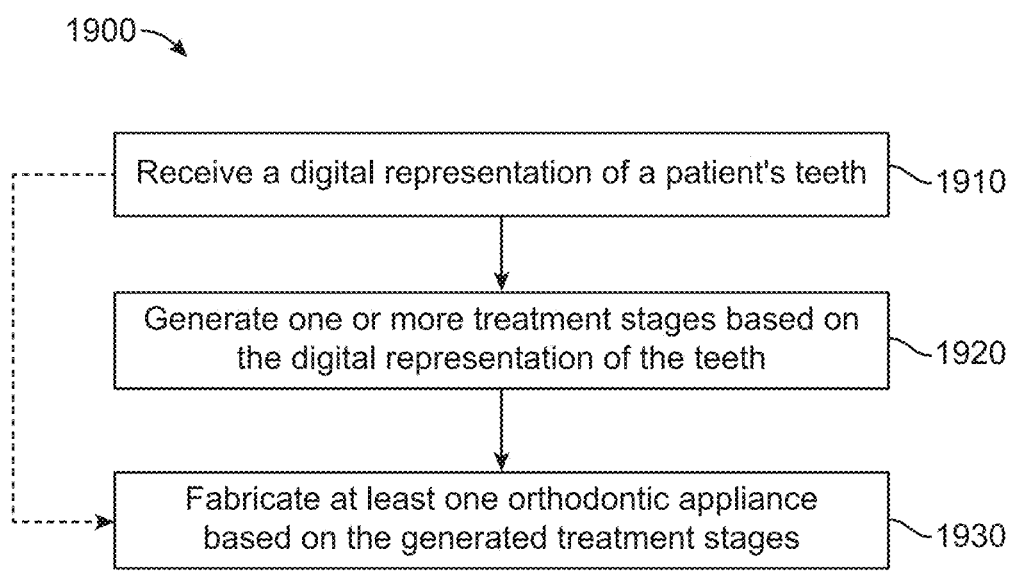
FIG. 18 illustrates a method for planning an orthodontic treatment, in accordance with one or more embodiments herein.

FIG. 18 illustrates a method 1900 for digitally planning an orthodontic treatment and/or design or fabrication of an appliance, in accordance with embodiments. The method 1900 can be applied to any of the treatment procedures described herein and can be performed by any suitable data processing system.

In block 1910, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 1920, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 1930, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 18, design and/or fabrication of an orthodontic appliance, and perhaps a particular orthodontic treatment, may include use of a representation of the patient's teeth (e.g., receive a digital representation of the patient's teeth 1910), followed by design and/or fabrication of an orthodontic appliance based on a representation of the patient's teeth in the arrangement represented by the received representation.

Optionally, some or all of the blocks of the method 1900 are performed locally at the site where the patient is being treated and during a single patient visit, referred to herein as "chair side manufacturing." Chair side manufacturing can involve, for example, scanning the patient's teeth, automatically generating a treatment plan with treatment stages, and immediately fabricating one or more orthodontic appliance(s) to treat the patient using a chair side direct fabrication machine, all at the treating professional's office during a single appointment. In embodiments where a series of appliances are used to treat the patient, the first appliance may be produced chair side for immediate delivery to the patient, with the remaining appliances produced separately (e.g., off site at a lab or central manufacturing facility) and delivered at a later time (e.g., at a follow up appointment, mailed to the patient). Alternatively, the methods herein can accommodate production and immediate delivery of the entire series of appliances on site during a single visit. Chair side manufacturing can thus improve the convenience and speed of the treatment procedure by allowing the patient to immediately begin treatment at the practitioner's office, rather than having to wait for fabrication and delivery of the appliances at a later date. Additionally, chair side manufacturing can provide improved flexibility and efficiency of orthodontic treatment. For instance, in some embodiments, the patient is re-scanned at each appointment to determine the actual positions of the teeth, and the treatment plan is updated accordingly. Subsequently, new appliances can be immediately produced and delivered chair side to accommodate any changes to or deviations from the treatment plan.

Figure 19:
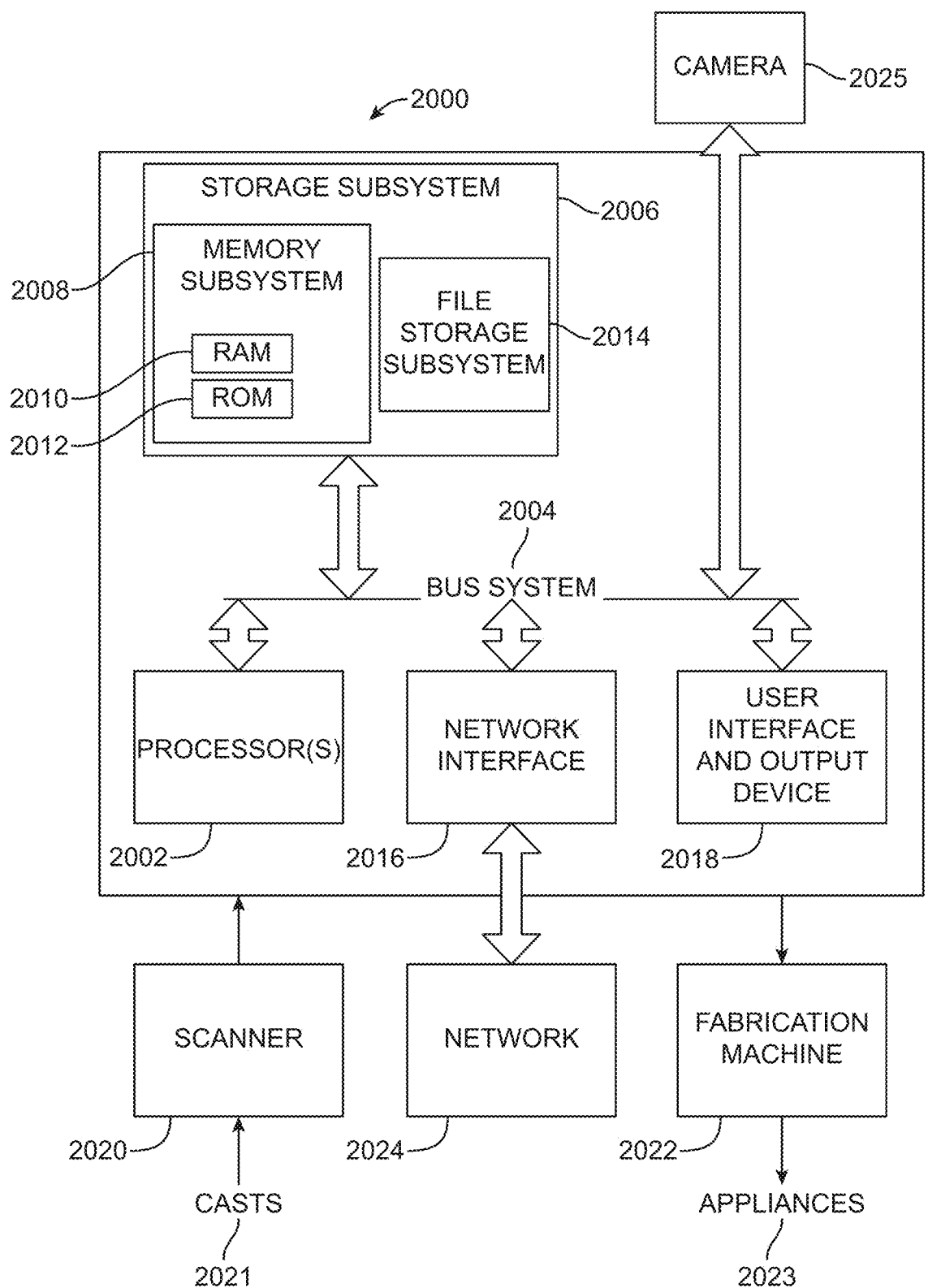
FIG. 19 is a simplified block diagram of a system for designing an orthodontic appliance and planning an orthodontic treatment, in accordance with one or more embodiments herein.

FIG. 19 is a simplified block diagram of a data processing system 2000 that may be used in executing methods and processes described herein. The data processing system 2000 typically includes at least one processor 2002 that communicates with one or more peripheral devices via bus subsystem 2004. These peripheral devices typically include a storage subsystem 2006 (memory subsystem 2008 and file storage subsystem 2014), a set of user interface input and output devices 2018, and an interface to outside networks 2016. This interface is shown schematically as "Network Interface" block 2016, and is coupled to corresponding interface devices in other data processing systems via communication network interface 2024. Data processing system 2000 can include, for example, one or more computers, such as a personal computer, workstation, mainframe, laptop, and the like.

The user interface input devices 2018 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 2006 maintains the basic required programming, including computer readable media having instructions (e.g., operating instructions, etc.), and data constructs. The program modules discussed herein are typically stored in storage subsystem 2006. Storage subsystem 2006 typically includes memory subsystem 2008 and file storage subsystem 2014. Memory subsystem 2008 typically includes a number of memories (e.g., RAM 2010, ROM 2012, etc.) including computer readable memory for storage of fixed instructions, instructions and data during program execution, basic input/output system, etc. File storage subsystem 2014 provides persistent (non-volatile) storage for program and data files, and can include one or more removable or fixed drives or media, hard disk, floppy disk, CD-ROM, DVD, optical drives, and the like. One or more of the storage systems, drives, etc., may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 2020 includes any means for obtaining a digital representation (e.g., images, surface topography data, etc.) of a patient's teeth (e.g., by scanning physical models of the teeth such as casts 2021, by scanning impressions taken of the teeth, or by directly scanning the intraoral cavity), which can be obtained either from the patient or from treating professional, such as an orthodontist, and includes means of providing the digital representation to data processing system 2000 for further processing. Scanner 2020 may be located at a location remote with respect to other components of the system and can communicate image data and/or information to data processing system 2000, for example, via a network interface 2024. Fabrication system 2022 fabricates appliances 2023 based on a treatment plan, including data set information received from data processing system 2000. Fabrication machine 2022 can, for example, be located at a remote location and receive data set information from data processing system 2000 via network interface 2024. The camera 2025 may include any image capture device configured to capture still images or movies. The camera 2025 may facilitate capturing various perspectives of a patient's dentition. In some implementations, the camera 2025 may facilitate capture of images at various focal lengths and distances from the patient.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing blocks can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein.

As used herein the terms "dental appliance," and "tooth receiving appliance" are treated synonymously. As used herein, a "dental positioning appliance" or an "orthodontic appliance" may be treated synonymously, and may include any dental appliance configured to change the position of a patient's teeth in accordance with a plan, such as an orthodontic treatment plan. A "patient," as used herein may include any person, including a person seeking dental/orthodontic treatment, a person undergoing dental/orthodontic treatment, and a person who has previously undergone dental/orthodontic treatment. A "patient" may include a customer or a prospective customer of orthodontic treatment, such as a person who is using the visualization tools herein to inform a decision to undergo orthodontic treatment at all or a decision to select a specific orthodontic treatment plan. A "dental positioning appliance" or "orthodontic appliance," as used herein, may include a set of dental appliances configured to incrementally change the position of a patient's teeth over time. As noted herein, dental positioning appliances and/or orthodontic appliances may comprise polymeric appliances configured to move a patient's teeth in accordance with an orthodontic treatment plan.

As used herein the term "and/or" may be used as a functional word to indicate that two words or expressions are to be taken together or individually. For example, the phrase "A and/or B" encompasses A alone, B alone, and A and B together. Depending on context, the term "or" need not exclude one of a plurality of words/expressions. As an example, the phrase "A or B" need not exclude A and B together.

As used herein the terms "torque" and "moment" are treated synonymously.

As used herein a "moment" may encompass a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example. Any discussion herein referring to application of forces on a patient's teeth is equally applicable to application of moments on the teeth, and vice-versa.

As used herein a "plurality of teeth" may encompass two or more teeth. A plurality of teeth may, but need not, comprise adjacent teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The embodiments disclosed herein may be well suited for moving one or more teeth of the first group of one or more teeth or moving one or more of the second group of one or more teeth, and combinations thereof.

The embodiments disclosed herein may be well suited for combination with one or more commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

Repositioning of teeth may be accomplished with the use of a series of removable elastic positioning appliances such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration. Repositioning of teeth may be accomplished through other series of removable orthodontic and/or dental appliances, including polymeric shell appliances.

A computer system, as used in this paper, is intended to be construed broadly. In general, a computer system will include a processor, memory, non-volatile storage, and an interface. A typical computer system will usually include at least a processor, memory, and a device (e.g., a bus) coupling the memory to the processor. The processor can be, for example, a general-purpose central processing unit (CPU), such as a microprocessor, or a special-purpose processor, such as a microcontroller.

The memory can include, by way of example but not limitation, random access memory (RAM), such as dynamic RAM (DRAM) and static RAM (SRAM). The memory can be local, remote, or distributed. The bus can also couple the processor to non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software on the computer system. The non-volatile storage can be local, remote, or distributed. The non-volatile storage is optional because systems can be created with all applicable data available in memory.

Software is typically stored in the non-volatile storage. Indeed, for large programs, it may not even be possible to store the entire program in the memory. Nevertheless, it should be understood that for software to run, if necessary, it is moved to a computer-readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at an applicable known or convenient location (from non-volatile storage to hardware registers) when the software program is referred to as "implemented in a computer-readable storage medium." A processor is considered to be "configured to execute a program" when at least one value associated with the program is stored in a register readable by the processor.

In one example of operation, a computer system can be controlled by operating system software, which is a software program that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus can also couple the processor to the interface. The interface can include one or more input and/or output (I/O) devices. Depending upon implementation-specific or other considerations, the I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device. The interface can include one or more of a modem or network interface. It will be appreciated that a modem or network interface can be considered to be part of the computer system. The interface can include an analog modem, ISDN modem, cable modem, token ring interface, satellite transmission interface (e.g. "direct PC"), or other interfaces for coupling a computer system to other computer systems. Interfaces enable computer systems and other devices to be coupled together in a network.

The computer systems can be compatible with or implemented as part of or through a cloud-based computing system. As used in this paper, a cloud-based computing system is a system that provides virtualized computing resources, software and/or information to end user devices. The computing resources, software and/or information can be virtualized by maintaining centralized services and resources that the edge devices can access over a communication interface, such as a network. "Cloud" may be a marketing term and for the purposes of this paper can include any of the networks described herein. The cloud-based computing system can involve a subscription for services or use a utility pricing model. Users can access the protocols of the cloud-based computing system through a web browser or other container application located on their end user device.

A computer system can be implemented as an engine, as part of an engine or through multiple engines. As used in this paper, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the FIGS. in this paper.

The engines described in this paper, or the engines through which the systems and devices described in this paper can be implemented, can be cloud-based engines. As used in this paper, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used in this paper, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described in this paper.

Datastores can include data structures. As used in this paper, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described in this paper, can be cloud-based datastores. A cloud based datastore is a datastore that is compatible with cloud-based computing systems and engines.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining. Additionally, though reference is made herein to orthodontic appliances, at least some of the techniques described herein may apply to restorative and/or other dental appliances, including without limitation crowns, veneers, teeth-whitening appliances, teeth-protective appliances, etc.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method of simulating orthodontic treatment, the method comprising:
    capturing a first 2D image, the first 2D image comprising a representation of a patient's face and a patient's teeth of a patient;
    identifying one or more shapes associated with at least one of the patient's teeth;
    building a parametric 3D model of the patient's teeth based on the 2D image, using one or more case-specific parameters for the one or more shapes associated with the at least one of the patient's teeth;
    simulating an outcome of a dental treatment plan for the patient's teeth to produce a simulated outcome of the dental treatment plan;
    modifying the parametric 3D model to provide a modified 3D model representing the simulated outcome of the dental treatment plan; and
    rendering, using the modified 3D model, a second 2D image representing the patient's face, the second 2D image representing the patient's teeth in accordance with the simulated outcome of the dental treatment plan.

2. The computer-implemented method of claim 1, wherein building the parametric 3D model includes:
    finding edges of teeth and lips in the first 2D image;
    aligning a parametric tooth model to the edges of the teeth and lips in the first 2D image to determine the case-specific parameters; and
    storing the case-specific parameters of the parametric tooth model that align the parametric tooth model with the edges of the teeth, gingiva, and lips in the first 2D image.

3. The computer-implemented method of claim 1, wherein rendering the second 2D image includes:
    accessing the parametric 3D model of the patient's teeth;
    projecting one or more teeth positions from the first 2D image onto the parametric 3D model;
    mapping color data from the 2D image to corresponding locations on the parametric 3D model to generate textures for the parametric 3D model; and using the textures as part of the second 2D image of the patient's face.

4. The computer-implemented method of claim 1, simulating an outcome of the dental treatment plan provides a predetermined position of the patients' teeth, and wherein the predetermined position is based on an average position of a plurality of previous patients' teeth after dental treatment.

5. The computer-implemented method of claim 1, simulating an outcome of the dental treatment plan provides a predetermined position of the patients' teeth, and wherein the predetermined position is based on an average position of a plurality of previous patients' teeth before dental treatment.

6. The computer-implemented method of claim 2, further comprising:
aligning the parametric 3D tooth model to the edges of the teeth, gingiva, and lips in the first 2D image.

7. The computer-implemented method of claim 1, wherein the first 2D image comprises a profile image representing a profile of the patient's face.

8. The computer-implemented method of claim 1, wherein the simulated outcome of the dental treatment plan comprises an estimated outcome of the dental treatment plan.

9. The computer-implemented method of claim 1, wherein the simulated outcome of the dental treatment plan comprises an intended outcome of the dental treatment plan.

10. The computer-implemented method of claim 1, wherein the dental treatment plan comprises an orthodontic treatment plan, a restorative treatment plan, or some combination thereof.

11. The computer-implemented method of claim 1, wherein capturing the first 2D image comprises: instructing a mobile phone or a camera to image the patient's face, or gathering the first 2D image from a storage device or a networked system.

12. The computer-implemented method of claim 1, wherein building the parametric 3D model of the patient's teeth based on the 2D image, using one or more case-specific parameters for the one or more shapes associated with the at least one of the patient's teeth comprises:
coarsely aligning teeth represented in the 3D parametric model to the patient's teeth represented in the 2D image; and
executing an expectation step to determine a probability that a projection of a silhouette of the 3D parametric model matches one or more edges of the 2D image a first time.

13. The computer-implemented method of claim 12, wherein building the parametric 3D model of the patient's teeth based on the 2D image, using one or more case-specific parameters for the one or more shapes associated with the at least one of the patient's teeth comprises:
executing a maximization step using a small angle approximation to linearize the rigid transformation of the teeth in the 3D model; and
executing the expectation step to determine a probability that a projection of a silhouette of the 3D parametric model matches the edges of the 2D image a second time.

14. The computer-implemented method of claim 13, further comprising:
iterating though the expectation and maximization steps a first plurality of times to with a first subset of parameters; and
after iterating though the expectation and maximization steps the first plurality of times with the first subset of parameters of the 3D parametric model, iterating though the expectation and maximization steps a second plurality of times with the first and second subset of parameters.

15. A computer-implemented method of building a 3D model of teeth from a 2D image, the method comprising:
capturing a 2D image of a patient's face, including their teeth;
determining edges of teeth and gingiva within the first 2D image;
fitting the teeth in a 3D parametric model of teeth to the edges of the teeth and gingiva within the first 2D image, the 3D parametric model including case-specific parameters for the shape of the patient's teeth; and
determining the value of the case-specific parameters of the 3D parametric model based on the fitting.

16. The computer-implemented method of claim 15, wherein:
fitting the teeth in the 3D parametric model of teeth to the edges of the teeth and gingiva within the first 2D image comprises:
coarsely aligning the teeth in the 3D parametric model to the teeth in the 2D image; and
executing an expectation step to determine a probability that a projection of a silhouette of the 3D parametric model matches the edges of the 2D image.

17. The computer-implemented method of claim 16, wherein:
fitting the teeth in the 3D parametric model of teeth to the edges of the teeth and gingiva within the first 2D image further comprises:
executing a maximization step using a small angle approximation to linearize the rigid transformation of the teeth in the model; and
executing the expectation step to determine a probability that a projection of a silhouette of the 3D parametric model matches the edges of the 2D image again.

18. The computer-implemented method of claim 17, further comprising:
iterating though the expectation and maximization steps a first plurality of times to with a first subset of parameters; and
after iterating though the expectation and maximization steps the first plurality of times with the first subset of parameters of the 3D parametric model, iterating though the expectation and maximization steps the second plurality of times with the first and second subset of parameters.

19. The computer-implemented method of claim 18, wherein the first plurality of time is the same as the second plurality of times.

20. The computer-implemented method of claim 18, wherein the first subset of case-specific parameters of the 3D parametric model are one or more of a scale factor and tooth location and orientation.

21. The computer-implemented method of claim 18, wherein the second subset of parameters of the 3D parametric model are one or more of a tooth shape and tooth location and orientation.

* * * * *